(12) United States Patent
Quadri et al.

(10) Patent No.: US 9,339,377 B2
(45) Date of Patent: May 17, 2016

(54) BODY CAVITY PROSTHESIS

(71) Applicant: Edwards Lifesciences CardiAQ LLC, Irvine, CA (US)

(72) Inventors: Arshad Quadri, West Hartford, CT (US); J. Brent Ratz, Winchester, MA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

(21) Appl. No.: 13/786,083

(22) Filed: Mar. 5, 2013

(65) Prior Publication Data

US 2013/0184813 A1     Jul. 18, 2013

Related U.S. Application Data

(63) Continuation of application No. 12/569,856, filed on Sep. 29, 2009, now Pat. No. 8,403,983.

(60) Provisional application No. 61/136,716, filed on Sep. 29, 2008.

(51) Int. Cl.
*A61F 2/848* (2013.01)
*A61F 2/24* (2006.01)

(52) U.S. Cl.
CPC ............... *A61F 2/2403* (2013.01); *A61F 2/24* (2013.01); *A61F 2/2409* (2013.01); *A61F 2/2412* (2013.01); *A61F 2/2415* (2013.01); *A61F 2/2418* (2013.01); *A61F 2210/0076* (2013.01); *A61F 2220/005* (2013.01); *A61F 2220/0075* (2013.01); *A61F 2230/0013* (2013.01); *A61F 2230/0054* (2013.01); *Y10T 29/49426* (2015.01)

(58) Field of Classification Search
CPC .................... A61F 2/844; A61F 2002/8483
USPC ................. 623/1.24, 1.36, 2.17, 2.4, 2.14
See application file for complete search history.

(56) References Cited

U.S. PATENT DOCUMENTS

| 4,477,930 A | 10/1984 | Totten et al. |
|---|---|---|
| 4,950,227 A | 8/1990 | Savin et al. |
| 5,067,957 A | 11/1991 | Jervis |
| 5,332,402 A | 7/1994 | Teitelbaum |
| 5,344,427 A | 9/1994 | Cottenceau et al. |

(Continued)

FOREIGN PATENT DOCUMENTS

| DE | 3128704 | 2/1983 |
|---|---|---|
| GB | 2245495 | 1/1992 |

(Continued)

OTHER PUBLICATIONS

International Search Report and Written Opinion for PCT/US2006/043526, mailed Jun. 25, 2008.

(Continued)

*Primary Examiner* — Thomas J Sweet
*Assistant Examiner* — Seema Mathew
(74) *Attorney, Agent, or Firm* — Knobbe Martens Olson & Bear LLP

(57) ABSTRACT

A prosthesis can be configured to be deployed within a body cavity. The prosthesis has an expandable frame, a plurality of proximal anchors, and a plurality of distal anchors, where the various anchors are connected to the frame. Radial expansion of the frame can cause the ends of the proximal anchors and the ends of the distal anchors to draw closer together.

26 Claims, 21 Drawing Sheets

(56) References Cited

U.S. PATENT DOCUMENTS

| | | | |
|---|---|---|---|
| 5,397,355 A * | 3/1995 | Marin et al. | 623/1.2 |
| 5,411,552 A | 5/1995 | Andersen et al. | |
| 5,474,563 A | 12/1995 | Myler et al. | |
| 5,509,930 A | 4/1996 | Love | |
| 5,575,818 A | 11/1996 | Pinchuk | |
| 5,607,469 A | 3/1997 | Frey | |
| 5,713,952 A | 2/1998 | Vanney et al. | |
| 5,725,519 A | 3/1998 | Penner et al. | |
| 5,810,873 A | 9/1998 | Morales | |
| 5,840,081 A | 11/1998 | Andersen et al. | |
| 5,855,601 A | 1/1999 | Bessler et al. | |
| 5,868,777 A * | 2/1999 | Lam | 606/194 |
| 5,876,437 A | 3/1999 | Vanney et al. | |
| 5,879,381 A | 3/1999 | Moriuchi et al. | |
| 5,902,334 A | 5/1999 | Dwyer et al. | |
| 5,935,108 A | 8/1999 | Katoh | |
| 5,954,764 A | 9/1999 | Parodi | |
| 5,957,949 A | 9/1999 | Leonhardt et al. | |
| 5,992,000 A | 11/1999 | Humphrey et al. | |
| 6,004,328 A | 12/1999 | Solar | |
| 6,015,431 A | 1/2000 | Thornton et al. | |
| 6,053,940 A | 4/2000 | Wijay | |
| 6,113,612 A | 9/2000 | Swanson et al. | |
| 6,132,458 A | 10/2000 | Staehle et al. | |
| 6,152,937 A * | 11/2000 | Peterson | A61K 17/11 606/153 |
| 6,159,237 A | 12/2000 | Alt | |
| 6,168,614 B1 | 1/2001 | Andersen et al. | |
| 6,168,616 B1 | 1/2001 | Brown, III | |
| 6,251,093 B1 | 6/2001 | Valley et al. | |
| 6,280,466 B1 | 8/2001 | Kugler et al. | |
| 6,312,465 B1 | 11/2001 | Griffin et al. | |
| 6,352,543 B1 | 3/2002 | Cole | |
| 6,425,916 B1 | 7/2002 | Garrison et al. | |
| 6,458,153 B1 | 10/2002 | Bailey et al. | |
| 6,475,237 B2 | 11/2002 | Drasler et al. | |
| 6,482,228 B1 | 11/2002 | Norred | |
| 6,511,491 B2 | 1/2003 | Grudem et al. | |
| 6,517,573 B1 | 2/2003 | Pollock | |
| 6,551,303 B1 | 4/2003 | Van Tassei et al. | |
| 6,582,462 B1 | 6/2003 | Andersen et al. | |
| 6,602,281 B1 | 8/2003 | Klein | |
| 6,641,606 B2 | 11/2003 | Ouriel et al. | |
| 6,676,698 B2 | 1/2004 | McGuckin et al. | |
| 6,695,878 B2 * | 2/2004 | McGuckin et al. | 623/1.19 |
| 6,712,836 B1 * | 3/2004 | Berg et al. | 606/213 |
| 6,723,123 B1 | 4/2004 | Kazatchkov et al. | |
| 6,730,118 B2 | 5/2004 | Spenser et al. | |
| 6,733,523 B2 | 5/2004 | Shaolian et al. | |
| 6,767,362 B2 | 7/2004 | Schreck | |
| 6,780,200 B2 | 8/2004 | Jansen | |
| 6,790,229 B1 | 9/2004 | Berreklouw | |
| 6,790,230 B2 | 9/2004 | Beyersdorf et al. | |
| 6,814,746 B2 | 11/2004 | Thompson et al. | |
| 6,858,034 B1 | 2/2005 | Hijlkema et al. | |
| 6,908,477 B2 | 6/2005 | McGuckin, Jr. et al. | |
| 6,908,481 B2 | 6/2005 | Cribier | |
| 6,926,732 B2 | 8/2005 | Derus et al. | |
| 6,936,058 B2 | 8/2005 | Forde et al. | |
| 6,979,350 B2 | 12/2005 | Moll et al. | |
| 7,018,401 B1 | 3/2006 | Hyodoh et al. | |
| 7,018,406 B2 | 3/2006 | Seguin et al. | |
| 7,044,966 B2 | 5/2006 | Svanidze et al. | |
| 7,087,088 B2 * | 8/2006 | Berg et al. | 623/23.64 |
| 7,147,661 B2 | 12/2006 | Chobotov et al. | |
| 7,147,663 B1 | 12/2006 | Berg et al. | |
| 7,186,265 B2 | 3/2007 | Sharkawy et al. | |
| 7,198,646 B2 * | 4/2007 | Figulla et al. | 623/2.1 |
| 7,201,772 B2 | 4/2007 | Schwammenthal et al. | |
| 7,252,682 B2 | 8/2007 | Seguin | |
| 7,276,084 B2 | 10/2007 | Yang et al. | |
| 7,329,278 B2 | 2/2008 | Seguin et al. | |
| 7,381,219 B2 | 6/2008 | Salahieh et al. | |
| 7,429,269 B2 | 9/2008 | Schwammenthal et al. | |
| 7,442,204 B2 | 10/2008 | Schwammenthal et al. | |
| 7,445,631 B2 | 11/2008 | Salahieh et al. | |
| 7,510,575 B2 | 3/2009 | Spenser et al. | |
| 7,527,646 B2 | 5/2009 | Rahdert et al. | |
| 7,585,321 B2 | 9/2009 | Cribier | |
| 7,628,805 B2 | 12/2009 | Spenser et al. | |
| 7,632,298 B2 | 12/2009 | Hijlkema et al. | |
| 7,682,390 B2 | 3/2010 | Seguin | |
| 7,708,775 B2 | 5/2010 | Rowe et al. | |
| 7,712,606 B2 | 5/2010 | Salahieh et al. | |
| 7,748,389 B2 | 7/2010 | Salahieh et al. | |
| 7,753,949 B2 | 7/2010 | Lamphere et al. | |
| 7,771,463 B2 | 8/2010 | Ton et al. | |
| 7,771,472 B2 | 8/2010 | Hendricksen et al. | |
| 7,780,725 B2 | 8/2010 | Haug et al. | |
| 7,803,185 B2 | 9/2010 | Gabbay | |
| 7,806,919 B2 | 10/2010 | Bloom et al. | |
| 7,815,673 B2 | 10/2010 | Bloom et al. | |
| 7,824,443 B2 | 11/2010 | Salahieh et al. | |
| 7,837,727 B2 | 11/2010 | Goetz et al. | |
| 7,846,203 B2 | 12/2010 | Cribier | |
| 7,871,435 B2 | 1/2011 | Carpentier | |
| 7,896,915 B2 | 3/2011 | Guyenot et al. | |
| 7,914,569 B2 | 3/2011 | Nguyen et al. | |
| 7,919,112 B2 | 4/2011 | Pathak et al. | |
| 7,947,075 B2 * | 5/2011 | Goetz et al. | 623/2.18 |
| 7,959,672 B2 | 6/2011 | Salahieh et al. | |
| 7,967,853 B2 | 6/2011 | Eidenschink et al. | |
| 7,972,377 B2 | 7/2011 | Lane | |
| 7,972,378 B2 | 7/2011 | Tabor et al. | |
| 7,981,151 B2 * | 7/2011 | Rowe | 623/2.1 |
| 7,993,394 B2 | 8/2011 | Hariton et al. | |
| 7,993,395 B2 | 8/2011 | Vanermen et al. | |
| 7,998,196 B2 | 8/2011 | Mathison | |
| 8,009,887 B2 | 8/2011 | Ionasec et al. | |
| 8,016,870 B2 | 9/2011 | Chew et al. | |
| 8,016,877 B2 | 9/2011 | Seguin et al. | |
| 8,029,564 B2 | 10/2011 | Johnson et al. | |
| 8,052,747 B2 | 11/2011 | Melnikov et al. | |
| 8,052,750 B2 | 11/2011 | Tuval et al. | |
| 8,057,538 B2 | 11/2011 | Bergin et al. | |
| 8,057,539 B2 | 11/2011 | Ghione et al. | |
| 8,057,540 B2 | 11/2011 | Letac et al. | |
| 8,062,350 B2 | 11/2011 | Gale et al. | |
| 8,062,359 B2 | 11/2011 | Marquez et al. | |
| 8,066,763 B2 | 11/2011 | Alt | |
| 8,070,799 B2 | 12/2011 | Righini et al. | |
| 8,070,800 B2 | 12/2011 | Lock et al. | |
| 8,070,801 B2 | 12/2011 | Cohn | |
| 8,070,802 B2 | 12/2011 | Lamphere et al. | |
| 8,075,611 B2 | 12/2011 | Millwee et al. | |
| 8,078,279 B2 | 12/2011 | Dennis et al. | |
| 8,080,054 B2 | 12/2011 | Rowe | |
| 8,083,793 B2 | 12/2011 | Lane et al. | |
| 8,088,158 B2 | 1/2012 | Brodeur | |
| 8,088,404 B2 | 1/2012 | Udipi et al. | |
| 8,092,520 B2 | 1/2012 | Quadri | |
| 8,100,964 B2 | 1/2012 | Spence | |
| 8,105,375 B2 | 1/2012 | Navia et al. | |
| 8,105,377 B2 | 1/2012 | Liddicoat | |
| 8,109,995 B2 | 2/2012 | Paniagua et al. | |
| 8,109,996 B2 | 2/2012 | Stacchino et al. | |
| 8,114,154 B2 | 2/2012 | Righini et al. | |
| 8,119,704 B2 | 2/2012 | Wang et al. | |
| 8,123,801 B2 | 2/2012 | Milo | |
| 8,128,681 B2 | 3/2012 | Shoemaker et al. | |
| 8,128,688 B2 | 3/2012 | Ding et al. | |
| 8,136,218 B2 | 3/2012 | Millwee et al. | |
| 8,137,398 B2 | 3/2012 | Tuval et al. | |
| 8,137,687 B2 | 3/2012 | Chen et al. | |
| 8,142,492 B2 | 3/2012 | Forster et al. | |
| 8,142,494 B2 | 3/2012 | Rahdert et al. | |
| 8,147,504 B2 | 4/2012 | Ino et al. | |
| 8,155,754 B2 | 4/2012 | Nygren et al. | |
| 8,157,852 B2 | 4/2012 | Bloom et al. | |
| 8,157,853 B2 | 4/2012 | Laske et al. | |
| 8,158,187 B2 | 4/2012 | Chen et al. | |
| 8,163,014 B2 | 4/2012 | Lane et al. | |
| 8,167,932 B2 | 5/2012 | Bourang et al. | |
| 8,167,934 B2 | 5/2012 | Styrc et al. | |

(56) References Cited

U.S. PATENT DOCUMENTS

| | | |
|---|---|---|
| 8,168,275 B2 | 5/2012 | Lee et al. |
| 8,170,645 B2 | 5/2012 | Solar et al. |
| 8,177,836 B2 | 5/2012 | Lee et al. |
| 8,180,428 B2 | 5/2012 | Kaiser et al. |
| 8,182,528 B2 | 5/2012 | Salahieh et al. |
| 8,182,829 B2 | 5/2012 | Kleiner et al. |
| 8,187,851 B2 | 5/2012 | Shah et al. |
| 8,195,293 B2 | 6/2012 | Limousin et al. |
| 8,202,529 B2 | 6/2012 | Hossainy et al. |
| 8,211,169 B2 | 7/2012 | Lane et al. |
| 8,219,229 B2 | 7/2012 | Cao et al. |
| 8,220,121 B2 | 7/2012 | Hendriksen et al. |
| 8,226,710 B2 | 7/2012 | Nguyen et al. |
| 8,231,930 B2 | 7/2012 | Castro et al. |
| 8,236,045 B2 | 8/2012 | Benichou et al. |
| 8,236,241 B2 | 8/2012 | Carpentier et al. |
| 8,241,274 B2 | 8/2012 | Keogh et al. |
| 8,246,677 B2 | 8/2012 | Ryan |
| 8,246,678 B2 | 8/2012 | Salahieh et al. |
| 8,252,051 B2 | 8/2012 | Chau et al. |
| 8,257,724 B2 | 9/2012 | Cromack et al. |
| 8,257,725 B2 | 9/2012 | Cromack et al. |
| 8,262,724 B2 | 9/2012 | Seguin et al. |
| 8,273,118 B2 | 9/2012 | Bergin |
| 8,273,120 B2 | 9/2012 | Dolan |
| 8,276,533 B2 | 10/2012 | Chambers et al. |
| 8,287,584 B2 | 10/2012 | Salahieh et al. |
| 8,287,591 B2 | 10/2012 | Keidar et al. |
| 8,303,653 B2 | 11/2012 | Bonhoeffer et al. |
| 8,308,798 B2 | 11/2012 | Pintor et al. |
| 8,313,520 B2 | 11/2012 | Barbut et al. |
| 8,313,525 B2 | 11/2012 | Tuval et al. |
| 8,323,335 B2 * | 12/2012 | Rowe et al. .................. 623/2.11 |
| 8,323,336 B2 | 12/2012 | Hill et al. |
| 8,337,541 B2 | 12/2012 | Quadri et al. |
| 8,348,995 B2 | 1/2013 | Tuval et al. |
| 8,349,001 B2 | 1/2013 | Mensah et al. |
| 8,349,003 B2 | 1/2013 | Shu et al. |
| 8,353,921 B2 | 1/2013 | Schaller et al. |
| 8,353,948 B2 | 1/2013 | Besselink et al. |
| 8,353,953 B2 | 1/2013 | Giannetti et al. |
| 8,357,387 B2 | 1/2013 | Dove et al. |
| 8,361,137 B2 * | 1/2013 | Perouse ...................... 623/1.15 |
| 8,361,537 B2 | 1/2013 | Shanley |
| 8,366,769 B2 | 2/2013 | Huynh et al. |
| 8,377,116 B2 | 2/2013 | Hsu et al. |
| 8,377,499 B2 | 2/2013 | Kleiner et al. |
| 8,382,816 B2 | 2/2013 | Pollock et al. |
| RE44,075 E | 3/2013 | Williamson et al. |
| 8,398,707 B2 | 3/2013 | Bergin |
| 8,403,983 B2 | 3/2013 | Quadri et al. |
| 8,409,274 B2 | 4/2013 | Li et al. |
| 8,414,635 B2 | 4/2013 | Hyodoh et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,430,902 B2 | 4/2013 | Bergheim |
| 8,430,927 B2 | 4/2013 | Bonhoeffer |
| 8,449,466 B2 | 5/2013 | Duhay et al. |
| 8,449,599 B2 | 5/2013 | Chau et al. |
| 8,454,684 B2 | 6/2013 | Bergin et al. |
| 8,460,335 B2 | 6/2013 | Carpenter |
| 8,460,365 B2 | 6/2013 | Haverkost et al. |
| 8,460,366 B2 | 6/2013 | Rowe |
| 8,460,370 B2 | 6/2013 | Zakay et al. |
| 8,460,373 B2 | 6/2013 | Fogarty et al. |
| 8,470,023 B2 | 6/2013 | Eidenschink et al. |
| 8,470,024 B2 | 6/2013 | Ghione et al. |
| 8,475,521 B2 | 7/2013 | Suri et al. |
| 8,475,522 B2 | 7/2013 | Jimenez et al. |
| 8,479,380 B2 | 7/2013 | Malewicz et al. |
| 8,480,730 B2 | 7/2013 | Maurer et al. |
| 8,480,731 B2 | 7/2013 | Elizondo et al. |
| 8,486,137 B2 | 7/2013 | Suri et al. |
| 8,500,688 B2 | 8/2013 | Engel et al. |
| 8,500,755 B2 | 8/2013 | Ino et al. |
| 8,500,798 B2 | 8/2013 | Rowe et al. |
| 8,500,801 B2 | 8/2013 | Eberhardt et al. |
| 8,500,802 B2 | 8/2013 | Lane et al. |
| 8,506,620 B2 | 8/2013 | Ryan |
| 8,506,625 B2 | 8/2013 | Johnson |
| 8,511,244 B2 | 8/2013 | Holecek et al. |
| 8,512,397 B2 | 8/2013 | Rolando et al. |
| 8,512,398 B2 | 8/2013 | Alkhatib |
| 8,512,399 B2 | 8/2013 | Lafontaine |
| 8,518,108 B2 | 8/2013 | Huynh et al. |
| 8,529,621 B2 | 9/2013 | Alfieri et al. |
| 8,535,368 B2 | 9/2013 | Headley, Jr. et al. |
| 8,539,662 B2 | 9/2013 | Stacchino et al. |
| 8,545,742 B2 | 10/2013 | Gada et al. |
| 8,551,162 B2 | 10/2013 | Fogarty et al. |
| 8,562,672 B2 | 10/2013 | Bonhoeffer et al. |
| 8,562,673 B2 | 10/2013 | Yeung et al. |
| 8,565,872 B2 | 10/2013 | Pederson |
| 8,568,472 B2 | 10/2013 | Marchand et al. |
| 8,579,964 B2 * | 11/2013 | Lane et al. .................... 623/2.11 |
| 8,579,965 B2 | 11/2013 | Bonhoeffer et al. |
| 8,585,756 B2 | 11/2013 | Bonhoeffer et al. |
| 8,591,570 B2 | 11/2013 | Revuelta et al. |
| 8,591,574 B2 | 11/2013 | Lambrecht et al. |
| 8,603,154 B2 | 12/2013 | Strauss et al. |
| 8,603,160 B2 | 12/2013 | Salahieh et al. |
| 8,603,161 B2 | 12/2013 | Drews et al. |
| 8,608,648 B2 | 12/2013 | Banik et al. |
| 8,617,236 B2 | 12/2013 | Paul et al. |
| 8,623,074 B2 | 1/2014 | Ryan |
| 8,623,080 B2 | 1/2014 | Fogarty et al. |
| 8,628,566 B2 | 1/2014 | Eberhardt et al. |
| 8,632,586 B2 | 1/2014 | Spenser |
| 8,632,608 B2 | 1/2014 | Carpentier et al. |
| 8,640,521 B2 | 2/2014 | Righini et al. |
| 8,641,639 B2 | 2/2014 | Manstrom et al. |
| 8,647,381 B2 | 2/2014 | Essinger et al. |
| 8,652,201 B2 | 2/2014 | Oberti et al. |
| 8,652,202 B2 | 2/2014 | Alon et al. |
| 8,652,203 B2 * | 2/2014 | Quadri et al. ................. 623/2.11 |
| 8,653,632 B2 | 2/2014 | Pederson et al. |
| 8,663,318 B2 | 3/2014 | Ho |
| 8,663,319 B2 | 3/2014 | Ho |
| 8,668,730 B2 | 3/2014 | McGuckin, Jr. et al. |
| 8,672,997 B2 | 3/2014 | Drasler et al. |
| 8,672,998 B2 | 3/2014 | Lichtenstein et al. |
| 8,672,999 B2 | 3/2014 | Cali et al. |
| 8,673,000 B2 | 3/2014 | Tabor et al. |
| 8,679,174 B2 | 3/2014 | Ottma et al. |
| 8,685,083 B2 | 4/2014 | Perier et al. |
| 8,685,086 B2 * | 4/2014 | Navia et al. .................. 623/2.18 |
| 8,690,787 B2 | 4/2014 | Blomqvist et al. |
| 8,690,936 B2 | 4/2014 | Nguyen et al. |
| 8,696,742 B2 | 4/2014 | Pintor et al. |
| 8,696,743 B2 | 4/2014 | Holecek et al. |
| 8,715,207 B2 | 5/2014 | Righini et al. |
| 8,715,337 B2 | 5/2014 | Chuter |
| 8,715,343 B2 | 5/2014 | Navia et al. |
| 8,721,713 B2 | 5/2014 | Tower et al. |
| 8,721,714 B2 | 5/2014 | Kelley |
| 8,728,154 B2 | 5/2014 | Alkhatib |
| 8,728,155 B2 * | 5/2014 | Montorfano et al. ........ 623/2.18 |
| 8,731,658 B2 | 5/2014 | Hampton et al. |
| 8,734,484 B2 | 5/2014 | Ahlberg et al. |
| 8,740,930 B2 | 6/2014 | Goodwin |
| 8,740,974 B2 | 6/2014 | Lambrecht et al. |
| 8,740,975 B2 | 6/2014 | Yang et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,814 B2 * | 7/2014 | Solem .......................... 623/1.14 |
| 8,764,820 B2 | 7/2014 | Dehdashtian et al. |
| 8,771,302 B2 | 7/2014 | Woolfson et al. |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,778,018 B2 | 7/2014 | Iobbi |

(56) References Cited

U.S. PATENT DOCUMENTS

| | | | |
|---|---|---|---|
| 8,784,478 B2 | 7/2014 | Tuval et al. | |
| 8,784,480 B2 | 7/2014 | Taylor et al. | |
| 8,790,387 B2 | 7/2014 | Nguyen et al. | |
| 8,790,395 B2 | 7/2014 | Straubinger et al. | |
| 8,790,396 B2 | 7/2014 | Bergheim et al. | |
| 8,791,171 B2 | 7/2014 | Pacetti | |
| 8,795,356 B2* | 8/2014 | Quadri et al. | 623/2.11 |
| 8,801,776 B2 | 8/2014 | House et al. | |
| 8,808,366 B2 | 8/2014 | Braido et al. | |
| 8,808,370 B2 | 8/2014 | Nitzan et al. | |
| 8,821,569 B2 | 9/2014 | Gurskis et al. | |
| 8,821,570 B2 | 9/2014 | DuMontelle et al. | |
| 8,828,078 B2 | 9/2014 | Salahieh et al. | |
| 8,828,079 B2 | 9/2014 | Thielen et al. | |
| 8,834,561 B2 | 9/2014 | Figulla et al. | |
| 8,834,564 B2 | 9/2014 | Tuval et al. | |
| 8,840,661 B2 | 9/2014 | Manasse | |
| 8,845,720 B2 | 9/2014 | Conklin | |
| 8,858,620 B2 | 10/2014 | Salahieh et al. | |
| 8,858,621 B2 | 10/2014 | Oba et al. | |
| 8,870,936 B2 | 10/2014 | Rowe | |
| 8,870,947 B2* | 10/2014 | Shaw | 623/1.36 |
| 8,870,948 B1 | 10/2014 | Erzberger et al. | |
| 8,876,712 B2 | 11/2014 | Yee et al. | |
| 8,876,883 B2 | 11/2014 | Rust | |
| 8,876,894 B2 | 11/2014 | Tuval et al. | |
| 8,876,895 B2 | 11/2014 | Tuval et al. | |
| 8,882,831 B2 | 11/2014 | Alkhatib | |
| 8,894,702 B2 | 11/2014 | Quadri et al. | |
| 8,894,703 B2 | 11/2014 | Salahieh et al. | |
| 8,906,081 B2 | 12/2014 | Cully et al. | |
| 8,911,455 B2* | 12/2014 | Quadri et al. | 606/139 |
| 8,911,844 B2 | 12/2014 | Ford | |
| 8,932,349 B2 | 1/2015 | Jenson et al. | |
| 8,940,887 B2 | 1/2015 | Chatterton et al. | |
| 8,945,208 B2 | 2/2015 | Jimenez et al. | |
| 8,945,210 B2 | 2/2015 | Cartledge et al. | |
| 8,951,280 B2 | 2/2015 | Cohn et al. | |
| 8,951,299 B2 | 2/2015 | Paul et al. | |
| 8,961,583 B2 | 2/2015 | Hojeibane et al. | |
| 8,961,589 B2 | 2/2015 | Kleiner et al. | |
| 8,961,595 B2 | 2/2015 | Alkhatib | |
| 8,968,393 B2 | 3/2015 | Rothstein | |
| 8,968,395 B2 | 3/2015 | Hauser et al. | |
| 8,979,922 B2 | 3/2015 | Jayasinghe et al. | |
| 8,986,713 B2 | 3/2015 | Cleek et al. | |
| 8,998,978 B2 | 4/2015 | Wang | |
| 8,998,981 B2 | 4/2015 | Tuval et al. | |
| 8,999,369 B2 | 4/2015 | Gale et al. | |
| 9,005,273 B2 | 4/2015 | Salahieh et al. | |
| 9,005,277 B2 | 4/2015 | Pintor et al. | |
| 9,011,521 B2 | 4/2015 | Haug et al. | |
| 9,011,524 B2 | 4/2015 | Eberhardt | |
| 9,011,528 B2 | 4/2015 | Ryan | |
| 9,023,100 B2 | 5/2015 | Quadri et al. | |
| 9,034,033 B2* | 5/2015 | McLean | A61F 2/2436 623/2.12 |
| 2001/0047200 A1* | 11/2001 | White et al. | 623/1.15 |
| 2002/0022853 A1 | 2/2002 | Swanson et al. | |
| 2002/0032481 A1* | 3/2002 | Gabbay | 623/2.11 |
| 2002/0111619 A1 | 8/2002 | Keast et al. | |
| 2003/0040792 A1 | 2/2003 | Gabbay | |
| 2003/0120263 A1* | 6/2003 | Ouriel et al. | 606/1 |
| 2003/0120333 A1* | 6/2003 | Ouriel et al. | 623/1.14 |
| 2003/0125797 A1* | 7/2003 | Chobotov et al. | 623/1.13 |
| 2003/0220683 A1 | 11/2003 | Minasian et al. | |
| 2004/0087900 A1 | 5/2004 | Thompson et al. | |
| 2004/0093058 A1* | 5/2004 | Cottone et al. | 623/1.11 |
| 2004/0102842 A1 | 5/2004 | Jansen | |
| 2004/0186561 A1 | 9/2004 | McGuckin, Jr. et al. | |
| 2004/0210304 A1 | 10/2004 | Seguin et al. | |
| 2004/0249433 A1 | 12/2004 | Freitag | |
| 2005/0033398 A1 | 2/2005 | Seguin | |
| 2005/0038470 A1 | 2/2005 | van der Burg et al. | |
| 2005/0090887 A1 | 4/2005 | Pryor | |
| 2005/0096738 A1 | 5/2005 | Cali et al. | |
| 2005/0125020 A1* | 6/2005 | Meade et al. | 606/191 |
| 2005/0137682 A1 | 6/2005 | Justino | |
| 2005/0137686 A1 | 6/2005 | Salahieh et al. | |
| 2005/0137687 A1 | 6/2005 | Salahieh et al. | |
| 2005/0137691 A1 | 6/2005 | Salahieh et al. | |
| 2005/0137693 A1 | 6/2005 | Haug et al. | |
| 2005/0137695 A1* | 6/2005 | Salahieh et al. | 623/2.11 |
| 2005/0137701 A1 | 6/2005 | Salahieh et al. | |
| 2005/0154444 A1 | 7/2005 | Quadri | |
| 2005/0182483 A1 | 8/2005 | Osborne et al. | |
| 2005/0203616 A1 | 9/2005 | Cribier | |
| 2005/0234546 A1* | 10/2005 | Nugent et al. | 623/2.11 |
| 2005/0283231 A1 | 12/2005 | Haug et al. | |
| 2006/0020334 A1 | 1/2006 | Lashinski et al. | |
| 2006/0052802 A1 | 3/2006 | Sterman et al. | |
| 2006/0052867 A1 | 3/2006 | Revuelta et al. | |
| 2006/0058872 A1 | 3/2006 | Salahieh et al. | |
| 2006/0064120 A1* | 3/2006 | Levine | A61F 2/04 606/153 |
| 2006/0095115 A1 | 5/2006 | Bladillah et al. | |
| 2006/0106454 A1 | 5/2006 | Osborne et al. | |
| 2006/0116625 A1* | 6/2006 | Renati et al. | 604/8 |
| 2006/0129235 A1* | 6/2006 | Seguin et al. | 623/2.11 |
| 2006/0149360 A1* | 7/2006 | Schwammenthal et al. | 623/1.36 |
| 2006/0161265 A1* | 7/2006 | Levine et al. | 623/23.65 |
| 2006/0195183 A1 | 8/2006 | Navia et al. | |
| 2006/0212110 A1 | 9/2006 | Osborne et al. | |
| 2006/0224232 A1* | 10/2006 | Chobotov | 623/1.16 |
| 2006/0253191 A1 | 11/2006 | Salahieh et al. | |
| 2006/0259135 A1 | 11/2006 | Navia et al. | |
| 2006/0259136 A1 | 11/2006 | Nguyen et al. | |
| 2006/0265056 A1 | 11/2006 | Nguyen et al. | |
| 2006/0287717 A1 | 12/2006 | Rowe et al. | |
| 2006/0287719 A1 | 12/2006 | Rowe et al. | |
| 2006/0293745 A1 | 12/2006 | Carpentier et al. | |
| 2007/0010876 A1 | 1/2007 | Salahieh et al. | |
| 2007/0016286 A1 | 1/2007 | Herrmann et al. | |
| 2007/0043435 A1 | 2/2007 | Seguin et al. | |
| 2007/0067016 A1 | 3/2007 | Jung | |
| 2007/0100432 A1* | 5/2007 | Case et al. | 623/1.15 |
| 2007/0118206 A1 | 5/2007 | Colgan et al. | |
| 2007/0118207 A1 | 5/2007 | Amplatz et al. | |
| 2007/0129794 A1* | 6/2007 | Realyvasquez | 623/2.11 |
| 2007/0162107 A1 | 7/2007 | Haug et al. | |
| 2007/0185559 A1 | 8/2007 | Shelso | |
| 2007/0213813 A1 | 9/2007 | Von Segesser et al. | |
| 2007/0219620 A1* | 9/2007 | Eells et al. | 623/1.13 |
| 2007/0233228 A1 | 10/2007 | Eberhardt et al. | |
| 2007/0250151 A1 | 10/2007 | Pereira | |
| 2007/0255391 A1 | 11/2007 | Hojeibane et al. | |
| 2007/0265656 A1* | 11/2007 | Amplatz | A61B 17/0057 606/200 |
| 2007/0270932 A1 | 11/2007 | Headley et al. | |
| 2007/0270937 A1 | 11/2007 | Leanna | |
| 2008/0009934 A1 | 1/2008 | Schneider et al. | |
| 2008/0021546 A1 | 1/2008 | Patz et al. | |
| 2008/0071363 A1 | 3/2008 | Tuval et al. | |
| 2008/0071366 A1 | 3/2008 | Tuval et al. | |
| 2008/0071369 A1* | 3/2008 | Tuval et al. | 623/2.38 |
| 2008/0082165 A1 | 4/2008 | Wilson et al. | |
| 2008/0082166 A1* | 4/2008 | Styrc et al. | 623/2.18 |
| 2008/0114441 A1* | 5/2008 | Rust et al. | 623/1.13 |
| 2008/0125859 A1 | 5/2008 | Salahieh et al. | |
| 2008/0133003 A1 | 6/2008 | Seguin | |
| 2008/0140189 A1 | 6/2008 | Nguyen et al. | |
| 2008/0147183 A1 | 6/2008 | Styrc | |
| 2008/0154358 A1 | 6/2008 | Tansley et al. | |
| 2008/0161911 A1* | 7/2008 | Revuelta et al. | 623/2.17 |
| 2008/0177381 A1 | 7/2008 | Navia et al. | |
| 2008/0208328 A1 | 8/2008 | Antocci et al. | |
| 2008/0221672 A1 | 9/2008 | Lamphere et al. | |
| 2008/0243245 A1* | 10/2008 | Thambar et al. | 623/2.11 |
| 2008/0255660 A1* | 10/2008 | Guyenot | A61F 2/2418 623/2.14 |
| 2008/0255661 A1 | 10/2008 | Straubinger et al. | |
| 2008/0262596 A1* | 10/2008 | Xiao | 623/1.14 |
| 2008/0262603 A1 | 10/2008 | Giaquinta et al. | |
| 2008/0269878 A1 | 10/2008 | Iobbi | |

(56) References Cited

U.S. PATENT DOCUMENTS

| | | | |
|---|---|---|---|
| 2008/0275549 A1 | 11/2008 | Rowe | |
| 2008/0288062 A1 | 11/2008 | Andrieu et al. | |
| 2008/0319526 A1 | 12/2008 | Hill et al. | |
| 2009/0005863 A1 | 1/2009 | Goetz et al. | |
| 2009/0054976 A1* | 2/2009 | Tuval et al. | 623/2.11 |
| 2009/0062908 A1* | 3/2009 | Bonhoeffer et al. | 623/1.24 |
| 2009/0076531 A1 | 3/2009 | Richardson et al. | |
| 2009/0076585 A1 | 3/2009 | Hendriksen | |
| 2009/0076598 A1 | 3/2009 | Salahieh et al. | |
| 2009/0112309 A1 | 4/2009 | Jaramillo et al. | |
| 2009/0118744 A1 | 5/2009 | Wells et al. | |
| 2009/0118824 A1 | 5/2009 | Samkov | |
| 2009/0118826 A1 | 5/2009 | Khaghani | |
| 2009/0125096 A1* | 5/2009 | Chu | A61F 2/07 623/1.14 |
| 2009/0132035 A1 | 5/2009 | Roth et al. | |
| 2009/0138079 A1 | 5/2009 | Tuval et al. | |
| 2009/0149946 A1 | 6/2009 | Dixon | |
| 2009/0163934 A1 | 6/2009 | Raschdorf et al. | |
| 2009/0171438 A1* | 7/2009 | Chuter et al. | 623/1.13 |
| 2009/0182407 A1 | 7/2009 | Leanna et al. | |
| 2009/0192601 A1 | 7/2009 | Rafiee et al. | |
| 2009/0216317 A1 | 8/2009 | Cromack et al. | |
| 2009/0222076 A1 | 9/2009 | Figulla et al. | |
| 2009/0248132 A1 | 10/2009 | Bloom et al. | |
| 2009/0248133 A1 | 10/2009 | Bloom et al. | |
| 2009/0258958 A1 | 10/2009 | Ford | |
| 2009/0264989 A1 | 10/2009 | Bonhoeffer et al. | |
| 2009/0264997 A1 | 10/2009 | Salahieh et al. | |
| 2009/0270972 A1* | 10/2009 | Lane | 623/1.14 |
| 2009/0276040 A1 | 11/2009 | Rowe et al. | |
| 2009/0281619 A1 | 11/2009 | Le et al. | |
| 2009/0287299 A1* | 11/2009 | Tabor et al. | 623/1.26 |
| 2009/0306768 A1 | 12/2009 | Quadri | |
| 2010/0004740 A1 | 1/2010 | Seguin et al. | |
| 2010/0036479 A1 | 2/2010 | Hill et al. | |
| 2010/0049306 A1 | 2/2010 | House et al. | |
| 2010/0082094 A1 | 4/2010 | Quadri et al. | |
| 2010/0094411 A1 | 4/2010 | Tuval et al. | |
| 2010/0114305 A1 | 5/2010 | Kang et al. | |
| 2010/0161027 A1* | 6/2010 | Orr | 623/1.13 |
| 2010/0179633 A1* | 7/2010 | Solem | 623/1.11 |
| 2010/0179647 A1 | 7/2010 | Carpenter et al. | |
| 2010/0191326 A1 | 7/2010 | Alkhatib | |
| 2010/0256723 A1 | 10/2010 | Murray | |
| 2010/0262157 A1 | 10/2010 | Silver et al. | |
| 2010/0274345 A1 | 10/2010 | Rust | |
| 2010/0298931 A1 | 11/2010 | Quadri et al. | |
| 2010/0312333 A1 | 12/2010 | Navia et al. | |
| 2011/0022157 A1* | 1/2011 | Essinger et al. | 623/1.26 |
| 2011/0022165 A1 | 1/2011 | Oba et al. | |
| 2011/0166644 A1 | 7/2011 | Keeble et al. | |
| 2011/0178597 A9 | 7/2011 | Navia et al. | |
| 2011/0224785 A1* | 9/2011 | Hacohen | 623/2.18 |
| 2011/0282438 A1 | 11/2011 | Drews et al. | |
| 2011/0301704 A1 | 12/2011 | Alfieri et al. | |
| 2011/0313515 A1* | 12/2011 | Quadri et al. | 623/2.2 |
| 2011/0319981 A1 | 12/2011 | Hill et al. | |
| 2011/0319989 A1* | 12/2011 | Lane et al. | 623/2.11 |
| 2012/0012487 A1 | 1/2012 | Tian et al. | |
| 2012/0016342 A1 | 1/2012 | Brecker | |
| 2012/0022605 A1 | 1/2012 | Jahns et al. | |
| 2012/0022639 A1 | 1/2012 | Hacohen et al. | |
| 2012/0022642 A1 | 1/2012 | Haug et al. | |
| 2012/0029627 A1 | 2/2012 | Salahieh et al. | |
| 2012/0035703 A1 | 2/2012 | Lutter et al. | |
| 2012/0035713 A1 | 2/2012 | Lutter et al. | |
| 2012/0041551 A1 | 2/2012 | Spenser et al. | |
| 2012/0059452 A1* | 3/2012 | Boucher et al. | 623/1.15 |
| 2012/0059454 A1 | 3/2012 | Millwee et al. | |
| 2012/0078353 A1* | 3/2012 | Quadri et al. | 623/2.11 |
| 2012/0078360 A1* | 3/2012 | Rafiee | A61F 2/2418 623/2.37 |
| 2012/0101571 A1 | 4/2012 | Thambar et al. | |
| 2012/0123529 A1 | 5/2012 | Levi et al. | |
| 2012/0179051 A1 | 7/2012 | Pfeiffer et al. | |
| 2012/0179239 A1 | 7/2012 | Quadri et al. | |
| 2012/0179243 A1 | 7/2012 | Yang et al. | |
| 2012/0185033 A1 | 7/2012 | Ryan | |
| 2012/0215303 A1* | 8/2012 | Quadri et al. | 623/2.18 |
| 2012/0259405 A1* | 10/2012 | Weber et al. | 623/1.15 |
| 2012/0259409 A1 | 10/2012 | Nguyen et al. | |
| 2012/0271398 A1 | 10/2012 | Essinger et al. | |
| 2012/0283820 A1 | 11/2012 | Tseng et al. | |
| 2012/0283824 A1 | 11/2012 | Lutter et al. | |
| 2012/0290062 A1* | 11/2012 | McNamara et al. | 623/1.2 |
| 2012/0310328 A1* | 12/2012 | Olson et al. | 623/1.26 |
| 2012/0323316 A1* | 12/2012 | Chau et al. | 623/2.18 |
| 2012/0330409 A1 | 12/2012 | Haug et al. | |
| 2013/0030418 A1* | 1/2013 | Taft | A61F 2/2418 606/1 |
| 2013/0030523 A1 | 1/2013 | Padala et al. | |
| 2013/0046378 A1 | 2/2013 | Millwee et al. | |
| 2013/0053949 A1 | 2/2013 | Pintor et al. | |
| 2013/0053950 A1 | 2/2013 | Rowe et al. | |
| 2013/0095264 A1 | 4/2013 | Sowinski et al. | |
| 2013/0096671 A1 | 4/2013 | Iobbi | |
| 2013/0110226 A1 | 5/2013 | Gurskis | |
| 2013/0110227 A1 | 5/2013 | Quadri et al. | |
| 2013/0110230 A1 | 5/2013 | Solem | |
| 2013/0116777 A1 | 5/2013 | Pintor et al. | |
| 2013/0131788 A1* | 5/2013 | Quadri et al. | 623/2.4 |
| 2013/0131793 A1 | 5/2013 | Quadri et al. | |
| 2013/0138203 A1 | 5/2013 | Quadri et al. | |
| 2013/0138207 A1 | 5/2013 | Quadri et al. | |
| 2013/0144375 A1* | 6/2013 | Giasolli et al. | 623/1.16 |
| 2013/0144378 A1 | 6/2013 | Quadri et al. | |
| 2013/0144380 A1 | 6/2013 | Quadri et al. | |
| 2013/0144381 A1 | 6/2013 | Quadri et al. | |
| 2013/0166024 A1 | 6/2013 | Drews et al. | |
| 2013/0172983 A1* | 7/2013 | Clerc et al. | 623/1.16 |
| 2013/0184814 A1 | 7/2013 | Huynh et al. | |
| 2013/0236889 A1 | 9/2013 | Kishimoto et al. | |
| 2013/0238087 A1 | 9/2013 | Taylor | |
| 2013/0245615 A1 | 9/2013 | Koltz | |
| 2013/0245736 A1 | 9/2013 | Alexander et al. | |
| 2013/0253635 A1 | 9/2013 | Straubinger et al. | |
| 2013/0253637 A1 | 9/2013 | Wang et al. | |
| 2013/0253639 A1 | 9/2013 | Alkhatib | |
| 2013/0253641 A1 | 9/2013 | Lattouf | |
| 2013/0253642 A1 | 9/2013 | Brecker | |
| 2013/0261737 A1* | 10/2013 | Costello | 623/2.11 |
| 2013/0261738 A1* | 10/2013 | Clague | A61F 2/2418 623/2.11 |
| 2013/0268069 A1 | 10/2013 | Zakai et al. | |
| 2013/0289695 A1 | 10/2013 | Tian et al. | |
| 2013/0304200 A1* | 11/2013 | McLean | A61F 2/2436 623/2.18 |
| 2013/0325098 A1 | 12/2013 | Desai et al. | |
| 2013/0325121 A1 | 12/2013 | Whatley et al. | |
| 2013/0331714 A1 | 12/2013 | Manstrom et al. | |
| 2013/0338764 A1 | 12/2013 | Thornton et al. | |
| 2013/0338765 A1 | 12/2013 | Braido et al. | |
| 2013/0345786 A1* | 12/2013 | Behan | 623/1.11 |
| 2013/0345803 A1 | 12/2013 | Bergheim, III | |
| 2014/0031930 A1 | 1/2014 | Keidar et al. | |
| 2014/0039612 A1 | 2/2014 | Dolan | |
| 2014/0039614 A1 | 2/2014 | Delaloye et al. | |
| 2014/0044689 A1 | 2/2014 | Liu et al. | |
| 2014/0046219 A1 | 2/2014 | Sauter et al. | |
| 2014/0046427 A1* | 2/2014 | Michalak | 623/1.12 |
| 2014/0052237 A1* | 2/2014 | Lane et al. | 623/2.11 |
| 2014/0081393 A1 | 3/2014 | Hasenkam et al. | |
| 2014/0086934 A1 | 3/2014 | Shams | |
| 2014/0088685 A1* | 3/2014 | Yevzlin et al. | 623/1.11 |
| 2014/0088694 A1 | 3/2014 | Rowe et al. | |
| 2014/0100420 A1 | 4/2014 | Mortier et al. | |
| 2014/0100651 A1* | 4/2014 | Kheradvar | A61B 17/0643 623/2.1 |
| 2014/0100653 A1 | 4/2014 | Savage et al. | |
| 2014/0107761 A1 | 4/2014 | Gale et al. | |
| 2014/0172085 A1 | 6/2014 | Quadri et al. | |
| 2014/0172086 A1 | 6/2014 | Quadri et al. | |
| 2014/0186417 A1 | 7/2014 | Trollsas et al. | |

(56) References Cited

U.S. PATENT DOCUMENTS

| | | | |
|---|---|---|---|
| 2014/0194978 A1 | 7/2014 | Seguin et al. | |
| 2014/0194981 A1 | 7/2014 | Menk et al. | |
| 2014/0194982 A1* | 7/2014 | Kovalsky | A61F 2/2412 623/2.38 |
| 2014/0194983 A1* | 7/2014 | Kovalsky et al. | 623/2.38 |
| 2014/0214154 A1 | 7/2014 | Nguyen et al. | |
| 2014/0214160 A1 | 7/2014 | Naor | |
| 2014/0215791 A1* | 8/2014 | Soundararajan | A61F 2/95 29/428 |
| 2014/0221823 A1 | 8/2014 | Keogh et al. | |
| 2014/0222136 A1* | 8/2014 | Geist | A61F 2/2466 623/2.11 |
| 2014/0222139 A1 | 8/2014 | Nguyen et al. | |
| 2014/0222142 A1* | 8/2014 | Kovalsky et al. | 623/2.17 |
| 2014/0249622 A1* | 9/2014 | Carmi | A61F 2/2442 623/2.11 |
| 2014/0256035 A1 | 9/2014 | Strasly et al. | |
| 2014/0257467 A1* | 9/2014 | Lane | A61F 2/2412 623/2.11 |
| 2014/0257475 A1* | 9/2014 | Gross | A61F 2/2439 623/2.38 |
| 2014/0277390 A1* | 9/2014 | Ratz et al. | 623/1.26 |
| 2014/0277402 A1 | 9/2014 | Essinger et al. | |
| 2014/0277422 A1* | 9/2014 | Ratz et al. | 623/2.37 |
| 2014/0277423 A1 | 9/2014 | Alkhatib et al. | |
| 2014/0277427 A1* | 9/2014 | Ratz et al. | 623/2.38 |
| 2014/0296975 A1 | 10/2014 | Tegels et al. | |
| 2014/0309731 A1 | 10/2014 | Quadri et al. | |
| 2014/0324164 A1 | 10/2014 | Gross et al. | |
| 2014/0350565 A1* | 11/2014 | Yacoby | A61F 2/2412 606/108 |
| 2014/0356519 A1 | 12/2014 | Hossainy et al. | |
| 2014/0364404 A1 | 12/2014 | Cleek et al. | |
| 2014/0364944 A1 | 12/2014 | Lutter et al. | |
| 2014/0370071 A1 | 12/2014 | Chen et al. | |
| 2015/0018944 A1* | 1/2015 | O'Connell | A61F 2/2427 623/2.42 |
| 2015/0032153 A1 | 1/2015 | Quadri et al. | |
| 2015/0045881 A1* | 2/2015 | Lim | A61F 2/2418 623/2.38 |
| 2015/0086603 A1 | 3/2015 | Hossainy et al. | |
| 2015/0088252 A1 | 3/2015 | Jenson et al. | |
| 2015/0105856 A1 | 4/2015 | Rowe et al. | |
| 2015/0142103 A1 | 5/2015 | Vidlund | |
| 2015/0148731 A1* | 5/2015 | McNamara | A61M 27/002 604/9 |
| 2015/0209141 A1* | 7/2015 | Braido | A61F 2/2418 623/2.17 |
| 2015/0216653 A1* | 8/2015 | Freudenthal | A61F 2/2418 623/2.17 |
| 2016/0038281 A1* | 2/2016 | Delaloye | A61F 2/2418 623/2.18 |

FOREIGN PATENT DOCUMENTS

| | | |
|---|---|---|
| GB | 2 398 245 | 8/2004 |
| WO | WO 97/49355 | 12/1997 |
| WO | WO 00/61034 | 10/2000 |
| WO | WO 01/35870 | 5/2001 |
| WO | WO 02/36048 | 5/2002 |
| WO | WO 03/092554 | 11/2003 |
| WO | WO 2005/011534 | 2/2005 |
| WO | WO 2005/087140 | 9/2005 |
| WO | WO 2006/089236 | 8/2006 |
| WO | WO 2007/123658 | 11/2007 |
| WO | WO 2008/091515 | 7/2008 |
| WO | WO 2008/103722 | 8/2008 |
| WO | WO 2008/150529 | 12/2008 |
| WO | WO 2009/045331 | 4/2009 |
| WO | WO 2009/052188 | 4/2009 |
| WO | WO 2009/091509 | 7/2009 |
| WO | WO 2009/134701 | 11/2009 |
| WO | WO 2009/137359 | 11/2009 |
| WO | WO 2009/155561 | 12/2009 |
| WO | WO 2010/008549 | 1/2010 |
| WO | WO 2010/098857 | 9/2010 |
| WO | WO 2010/138853 | 12/2010 |
| WO | WO 2009/149462 | 1/2011 |

OTHER PUBLICATIONS

International Search Report and Written Opinion for PCT/US2009/058893, mailed Dec. 11, 2009.
European Extended Search Report for EP App. No. EP 06 82 7638, dated Feb. 28, 2013.
International Search Report and Written Opinion for PCT/US2010/031313, mailed Dec. 22, 2010.
U.S. Appl. No. 14/197,590, filed Mar. 5, 2014, Ratz et al.
U.S. Appl. No. 14/197,639, filed Mar. 5, 2014, Ratz et al.
U.S. Appl. No. 14/197,690, filed Mar. 5, 2014, Ratz et al.
U.S. Appl. No. 29/484,001, filed Mar. 5, 2014, Pesce et al.
CardiAQ Valve Technologies, "Innovations in Heart Valve Therapy," In3 San Francisco, Jul. 18, 2008, PowerPoint presentation in 19 slides.
Neovasc Surgical Products, "Neovasc Surgical Products: An Operating Division of Neovasc Inc.," dated Apr. 2009.
Kronemyer, Bob: "CardiAQ Valve Technologies: Percutaneous Mitral Valve Replacement," Start Up—Windhover Review of Emerging Medical Ventures, vol. 14, No. 6, Jun. 2009, pp. 48-49.
Bavaria, Joseph E. M.D.: "CardiAQ Valve Technologies: Transcatheter Mitral Valve Implantation," Sep. 21, 2009.
CardiAQ's Objection in Patent Vindication Action in regard to EP 2 566 416; Administrative Court of Munich; *CardiAQ Valve Technologies, Inc., v. Neovasc Tiara Inc.*; filed on Jun. 25, 2014.
Exhibits accompanying CardiAQ's Objection in Patent Vindication Action in regard to EP 2 566 416; filed on Jun. 25, 2014.
Neovasc's Statement of Defense in Patent Vindication Action in regard to EP 2 566 416; Administrative Court of Munich; *CardiAQ Valve Technologies, Inc., v. Neovasc Tiara Inc.*; filed on Dec. 9, 2014.
Exhibits accompanying Neovasc's Statement of Defense in Patent Vindication Action in regard to EP 2 566 416; filed on Dec. 9, 2014.
CardiAQ's Complaint and Jury Demand; U.S. District Court—District of Massachusetts; Case No. 1:14-cv-12405-ADB; *CardiAQ Valve, Technologies Inc. v. Neovasc Inc. and Neovasc Tiara Inc.*; filed Jun. 6, 2014.
CardiAQ's First Amended Complaint and Jury Demand; U.S. District Court—District of Massachusetts; Case No. 1:14-cv-12405-ADB; *CardiAQ Valve, Technologies Inc. v. Neovasc Inc. and Neovasc Tiara Inc.*; filed Aug. 12, 2014.
Court's Memorandum & Order; U.S. District Court—District of Massachusetts; Case No. 1:14-cv-12405-ADB; *CardiAQ Valve, Technologies Inc. v. Neovasc Inc. and Neovasc Tiara Inc.*; filed Nov. 6, 2014.
Defendants Neovasc Inc.'s and Neovasc Tiara Inc.'s Answer to Plaintiff's First Amended Complaint; U.S. District Court—District of Massachusetts; Case No. 1:14-cv-12405-ADB; *CardiAQ Valve, Technologies Inc. v. Neovasc Inc. and Neovasc Tiara Inc.*; filed Nov. 20, 2014.
CardiAQ's Second Amended Complaint and Jury Demand; U.S. District Court—District of Massachusetts; Case No. 1:14-cv-12405-ADB; *CardiAQ Valve, Technologies Inc. v. Neovasc Inc. and Neovasc Tiara Inc.*; filed Jan. 15, 2015.
Defendants Neovasc Inc.'s and Neovasc Tiara Inc.'s Answer to Plaintiff's Second Amended Complaint; U.S. District Court—District of Massachusetts; Case No. 1:14-cv-12405-ADB; *CardiAQ Valve, Technologies Inc. v. Neovasc Inc. and Neovasc Tiara Inc.*; filed Jan. 29, 2015.
U.S. Appl. No. 14/598,568, filed Jan. 16, 2015, Quadri et al.
U.S. Appl. No. 14/628,034, filed Feb. 20, 2015, Rabito et al.
U.S. Appl. No. 14/702,233, filed May 1, 2015, Arshad et al.
U.S. Appl. No. 14/716,507, filed May 19, 2015, Ratz et al.
U.S. Appl. No. 14/724,355, filed May 28, 2015, Rabito et al.
Grube et al.: "Percutaneous Implantation of the CoreValve Self-Expanding Valve Prosthesis in High-Risk Patients With Aortic Valve Disease," Valvular Heart Disease, circ.ahajournals.org (2006, 114:1616-1624). Published on line before print Oct. 2, 2006.

(56) References Cited

OTHER PUBLICATIONS

Businesswire.com, "50 Early-to Late-Stage Medical Device Companies Seeking Investment and Partnering Opportunities to Present in 3 Weeks at 'Investment in Innovation (In3) Medical Device Summit,'" May 27, 2008.

Ratz, J. Brent, "LSI EMT Spotlight," May 15, 2009.

"CVT's Transcatheter Mitral Valve Implantation (TMVI) platform might be the 'next big thing' in the cardiac cath lab," Jun. 2, 2009.

Ratz, J. Brent, "In3 Company Overview," Jun. 24, 2009.

"Company Overview," Jun. 25, 2009 at TVT.

Enhancedonlinenews,com, "CardiAQ Valve Technologies (CVT) Discloses Successful Results of Acute In Vivo Study of Its Novel Transcatheter Mitral Valve Implantation (TMVI) System," Sep. 28, 2009.

Neovasc's Statement of Defense in Patent Vindication Action in regard to EP 2 566 416; Regional Court of Munich; *CardiAQ Valve Technologies, Inc.*, v. *Neovasc Tiara Inc.*; filed on Dec. 9, 2014.

US 8,221,315, 07/2012, Lambrecht et al. (withdrawn)

\* cited by examiner

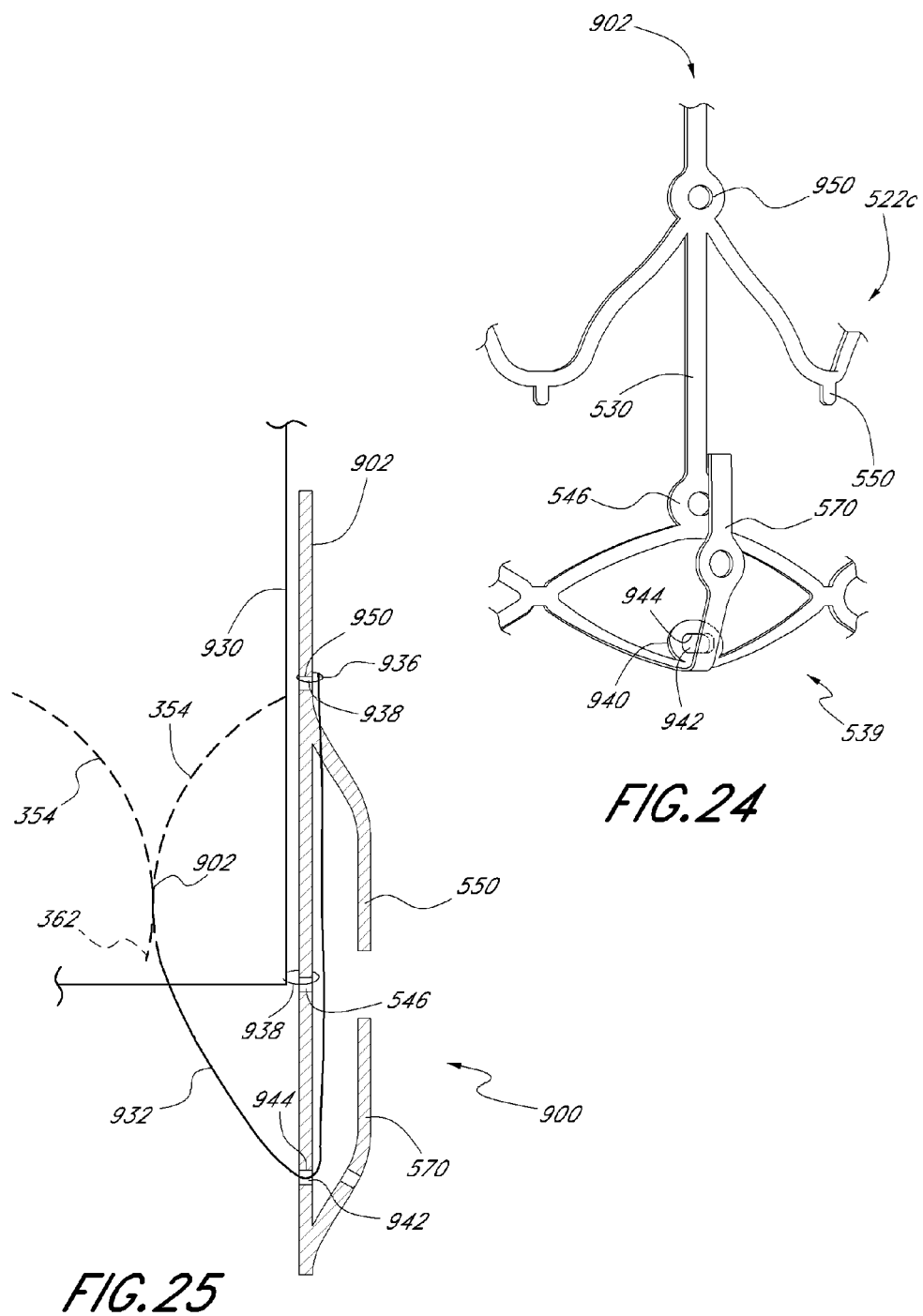

BODY CAVITY PROSTHESIS

CROSS-REFERENCE TO RELATED APPLICATIONS

This application is a continuation of U.S. application Ser. No. 12/569,856, filed Sep. 29, 2009, which claims priority to U.S. Provisional Appl. No. 61/136,716, which was filed on Sep. 29, 2008. U.S. application Ser. No. 12/569,856, published as US 2010/0082094 A1, is incorporated by reference herein in its entirety and is to be considered a part of this specification. Concerning Provisional Application No. 61/136,716, at least the portions describing embodiments of a tissue-based valve body formed from flat source material, manufacturing of same, and placement upon and use in conjunction with a stent, as discussed in paragraphs [00020]-[00027] and FIGS. 1A-8D are hereby incorporated by reference.

BACKGROUND

1. Field of the Invention

The present invention relates to prosthesis for use in body cavities. In some embodiments, the prosthesis can be a replacement heart valve.

2. Description of the Related Art

Human heart valves, which include the aortic, pulmonary, mitral and tricuspid valves, function essentially as one-way valves operating in synchronization with the pumping heart. The valves allow blood to flow in a downstream direction, but block blood from flowing in an upstream direction. Diseased heart valves exhibit impairments such as narrowing of the valve or regurgitation. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatus to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable stent that is then delivered to the native valve's annulus.

Development of replacement heart valves that can be compacted for delivery and then controllably expanded for controlled placement has proven to be particularly challenging. Further, durability concerns, particularly with tissue-based replacement valves, are at the forefront. For example, tissue-based valves typically include components that are sewn together, and such seams can be sources of stress concentrations, particularly when relatively thin tissue is used.

SUMMARY

Accordingly, there is in the need of the art for a tissue-based heart valve with enhanced durability and which lends itself to compaction and controlled expansion in a minimally invasive and/or percutaneous delivery.

In accordance with one embodiment, the present invention provides a replacement heart valve that comprises a valve body having an outer layer and an inner layer. The outer layer is tubular and has a longitudinal axis, an upstream end and a downstream end, and is formed from a thin, flexible material. The inner layer is generally tubular, has a longitudinal axis generally collinear with the outer layer, and is positioned within the tubular outer layer. The inner layer is formed from a thin, flexible material and defines a plurality of leaflets adapted to move between an open state and a coapted state. Each leaflet has a side edge and a downstream portion. Adjacent leaflets of the inner layer are connected by a commissural portion. The leaflets are attached to the outer layer along the leaflet side edges, and the commissural portions are attached to the outer layer downstream of at least a portion of the leaflet side edges;

In one such embodiment, the inner and outer layers are constructed from a single, contiguous section of the flexible material. In another embodiment, the inner and outer layers are folded relative to one another at the upstream end so that the inner layer is contiguous with the outer layer at the upstream end.

In another embodiment, the outer layer comprises a commissural slit, and an edge of one of the commissural portions of the inner layer extends at least partially through the slit. In one such embodiment, the outer layer comprises a leaflet slit shaped to complement a corresponding leaflet side edge, and the leaflet side edge extends at least partially through the slit.

In yet another embodiment, the outer layer has a plurality of windows formed therethrough, and the windows are configured so that, when the leaflets are in the coapted state, blood readily flows through the windows.

In a further embodiment, a replacement heart valve comprises a valve body and an elongate stent that can be radially compacted to a compacted state and radially expanded to an expanded state. The stent having a longitudinal axis and the valve body is attached to the stent.

In one such embodiment, an outer layer of the valve body is on an outer side of the stent and an inner layer of the valve body is on an inner side of the stent so that the stent is sandwiched between the inner and outer layers.

In another such embodiment, the valve body is positioned so that the stent is adjacent an outer surface of the valve body. In some such embodiments, an outer layer of the valve body is connected to the stent, and an inner layer of the valve body is directly connected to the outer layer, but is not directly connected to the stent. In additional such embodiments, when the leaflets are in an open position, an outer layer of the valve body is interposed between open leaflets and the stent.

In yet another such embodiment, the stent has a foreshortening portion, which foreshortening portion is configured so that as the stent is radially compacted, the foreshortening portion longitudinally expands, and as the stent is radially expanded, the foreshortening portion longitudinally contracts.

In one embodiment with such a foreshortening stent, at least a portion of the valve body is disposed at least partially within the foreshortening portion, and the valve body is attached to the stent at one or more connecting points, which connecting points are generally aligned with an axial point along the stent longitudinal axis, so that during foreshortening the stent longitudinally moves relative to the valve body without longitudinally stretching or crushing the valve body. One such embodiment additionally comprises a longitudinally expandable material that is directly connected to the stent and to the valve body. The flexible material is directly connected to the stent at one or more connection points that are longitudinally spaced from the axial point.

In another embodiment having a foreshortening stent, the stent additionally comprises a non-foreshortening portion, and a valve body is maintained within the non-foreshortening portion.

In accordance with another embodiment, the present invention provides a method of making a replacement heart valve. The method includes providing a flat, flexible source material and cutting the flat material according to a desired pattern. The pattern defines first and second pattern ends, a skirt portion, and a leaflet portion. The leaflet portion defines a plurality of leaflets, commissures extending between adjacent leaflets, and each leaflet having side edges. The method additionally comprises adjoining the first and second pattern ends so as to form the flat material into a tube, folding the leaflet portion relative to the skirt portion along a fold line so that the leaflet portion is generally within the skirt portion, attaching the commissures to the skirt portion, and attaching the leaflet side edges to the skirt portion.

Another embodiment additionally comprises providing a form having a shape that is substantially the negative of a desired shape of the valve in a closed state, the form having leaflet shaping portions, and after the flat material has been formed into a tube and the commissures attached to the skirt portion, placing the valve upon the form so that the leaflets engage the leaflet shaping portions, and attaching the leaflet side edges to the skirt portion when the leaflets are engaged with the leaflet shaping portions.

A further such embodiment additionally comprises forming leaflet slits in the skirt portion, the leaflet slits generally corresponding the a desired curvature of the leaflets, and placing the valve upon the form so that the leaflets engage the leaflet shaping portions comprises extending the leaflet side edges through the leaflet slits in the skirt portion.

Another embodiment additionally comprises providing an elongate stent, and attaching the skirt portion to the stent.

In accordance with still another embodiment, a method of treating valve insufficiency of a patient by delivering a replacement heart valve is provided. The method comprises providing a replacement heart valve comprising a valve body attached to a stent, the valve body having an upstream end and a plurality of leaflets adapted to open and close, the leaflets each having a downstream portion, the stent being elongate and having an upstream end, a downstream end, and a longitudinal midpoint halfway between the upstream and downstream ends, the stent having an annulus attachment zone adapted to engage a native valve annulus, the annulus attachment zone disposed at or adjacent the downstream end of the stent, and positioning the heart valve within a patient's heart so that the annulus attachment zone of the stent engages a patient's mitral annulus, and the longitudinal midpoint of the stent is disposed within the patient's left atrium.

In one such embodiment, the step of positioning the heart valve comprises positioning the valve so that substantially all of the stent is disposed in the patient's mitral annulus or left atrium.

In another embodiment, the valve body is connected to the stent so that the leaflets are substantially within the left atrium. In other embodiments, the valve body is connected to the stent so that the downstream ends of the leaflets are disposed generally within the mitral annulus.

In accordance with yet another embodiment, the present invention provides a flexible tubular valve body defining a plurality of leaflets connected to a longitudinally stretchable portion. The valve body is less longitudinally stretchable than the longitudinally stretchable portion. In one such embodiment, the valve body and connected longitudinally stretchable portion are mounted on a stent that has a foreshortening portion, and a portion of the valve body overlaps the foreshortening portion so the when the stent foreshortens, the longitudinally stretchable portion preferentially stretches or contracts so that the valve body moves longitudinally relative to the stent.

In another embodiment, a valve body having an inner layer and an outer layer, the inner layer defining a plurality of leaflets, is constructed by separately forming the inner and outer layers, attaching an upstream end of the inner layer to the outer layer, and attaching side edges and commissural tabs of the leaflets to the outer layer. In one such embodiment, slits are formed through the outer layer, and one or more of the commissural tabs and leaflets are drawn at least partially through corresponding slits and then secured to the outer layer.

Other inventive embodiments and features are disclosed below.

BRIEF DESCRIPTION OF THE DRAWINGS

FIG. 24 is a partial side view of a stent for use in accordance with the assembly of FIG. 23.

FIG. 25 is a schematic partial side view of a vertical cross-section of the heart valve of FIG. 24.

DETAILED DESCRIPTION OF PREFERRED EMBODIMENTS

The present specification and drawings disclose aspects and features of the invention in the context of several embodiments of replacement heart valves and portions thereof that are configured for replacement of natural heart valves in a patient. These embodiments may be discussed in connection with replacing specific valves such as the patient's aortic or mitral valve. However, it is to be understood that the context of a particular valve or particular features of a valve should not be taken as limiting, and features of any one embodiment discussed herein can be combined with features of other embodiments as desired and when appropriate.

Figure 1:
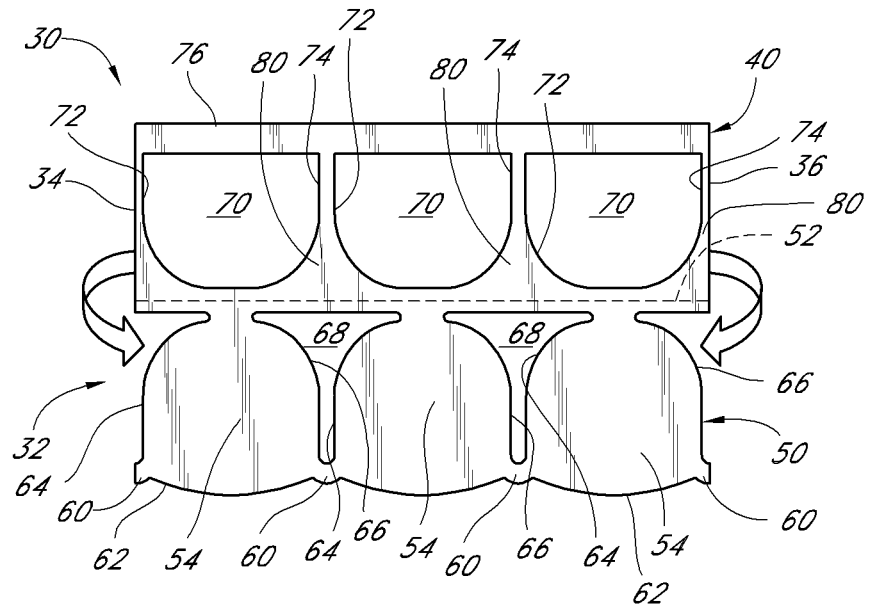
FIG. 1 illustrates a flat pattern for cutting a flat source material to create an embodiment of a heart valve body.

With initial reference to FIGS. 1-3, a structure for a heart valve body 30, along with methods of making the valve body 30, are described. In this embodiment, the heart valve body is constructed of a tissue-based media such as bovine pericardium. Of course, other materials such as equine and porcine pericardium, vascular tissue, as well as other natural and manmade materials that are thin, flexible and durable, may be employed. Preferably, the tissue is provided as a flat source material.

FIG. 1 illustrates a flat pattern 32 for cutting flat source tissue to form an embodiment of a heart valve body 30. More specifically, source tissue preferably is laid out in a flat format, and then cut according to the illustrated flat pattern 32. Preferably the tissue is cut by a laser, but other cutting modes and methods can be employed.

As illustrated in FIG. 1, the flat source tissue cut according to the pattern has first and second pattern ends 34, 36. A skirt portion 40 and a leaflet portion 50 are separated by a fold line 52. The illustrated leaflet portion 50 comprises three leaflets 54 connected to one another at commissural tab portions 60. Each leaflet 54 has a downstream edge 62 that preferably is curved, and also has curved, generally-opposing first and second leaflet side edges 64, 66. In accordance with the pattern 32 in the illustrated embodiment, the adjacent leaflets 54 are defined by voids 68 cut between them.

The illustrated skirt portion 40 comprises three windows 70 that are defined by apertures cut through the flat source tissue. The windows 70 each have first and second side edges 72, 74, which first and second window side edges 72, 74 are generally complementary in curvature to the first and second side edges 64, 66, respectively, of the corresponding leaflets 54. A downstream ring 76 of the skirt portion 40 preferably runs continuously from the first pattern end 34 to the second pattern end 36. Similarly, an upstream ring portion 78 of the flat pattern 32 runs continuously from the first pattern end 34 to the second pattern end 36 at and adjacent the fold line 52. Leaflet supports 80 are defined between adjacent windows 70, and share the first and second window side edges 72, 74. The leaflet supports 80 extend from the upstream ring 78 to the downstream ring 76. In the illustrated embodiment, the first and second pattern ends 34, 36 are arranged to evenly split one of the leaflet supports 80 of the skirt portion 40 and one of the commissural tab portions 60 of the leaflet portion 50.

Figure 2A:
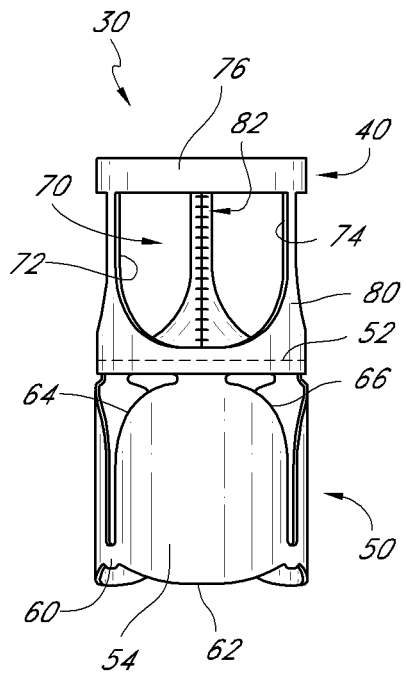
FIG. 2A is a side view of tissue cut according to the flat pattern of FIG. 1 and formed into a tube.
Figure 2B:
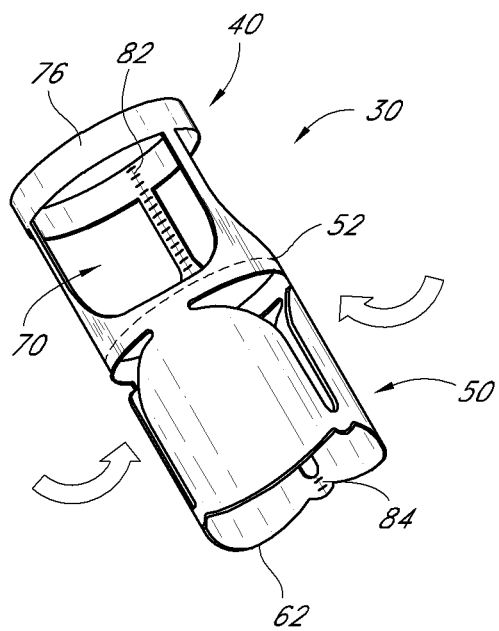
FIG. 2B is a perspective view of the assembly of FIG. 2A.

With reference to FIGS. 2A and 2B, once the pattern 32 has been cut from the flat source tissue, the cut tissue is rolled and the first and second pattern ends 34, 36 are joined together to create a tubular structure as shown. In the illustrated embodiment, the first and second pattern ends 34, 36 are joined together by a seam that preferably employs a conventional suture material. As such, a seam 82 in the skirt portion 40 connects the first and second pattern ends 34, 36 so as to complete the leaflet support 80, and a seam 84 in the leaflet portion 50 completes the commissural tab 6.

Although sutures are used in the illustrated embodiment, it is to be understood that other methods and apparatus can be used to join the first and second ends and to make other connections when forming valve bodies. For example, in other embodiments, adhesives, clips or the like may be employed.

Figure 3A:
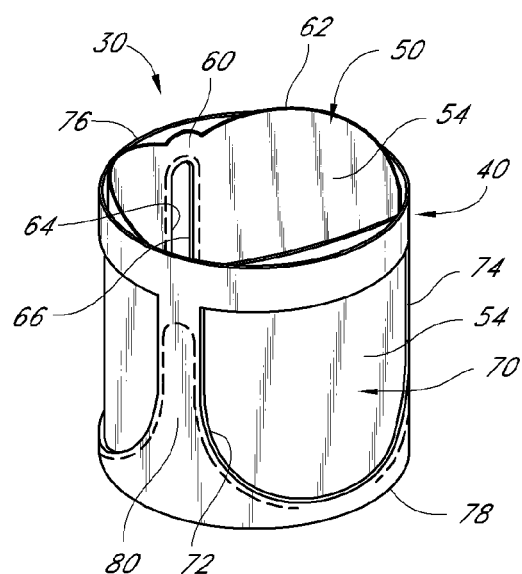
FIG. 3A is a perspective view of the assembly of FIG. 1 formed into a heart valve body and shown in an open position.
Figure 3B:
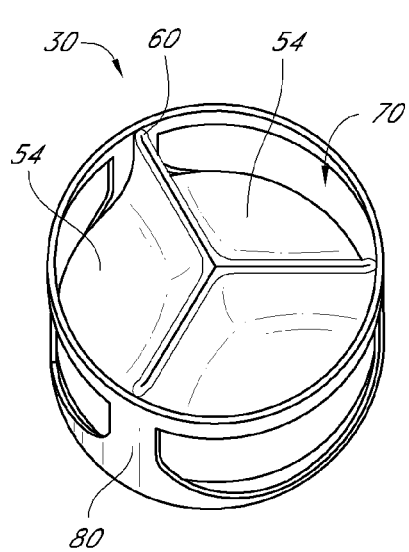
FIG. 3B shows the heart valve body of FIG. 3A in a closed condition and viewed from a downstream position.
Figure 3C:
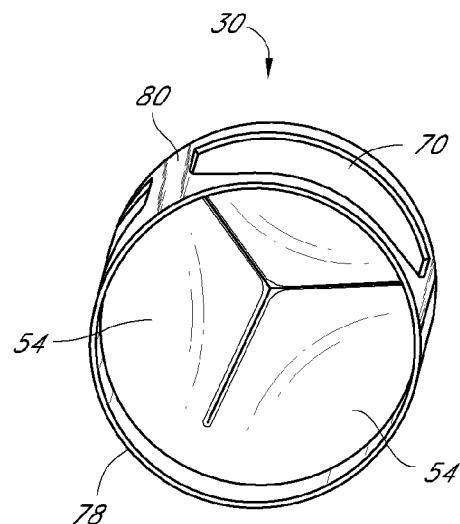
FIG. 3C shows the heart valve body of FIG. 3A in a closed condition and viewed from an upstream position.

With additional reference to FIGS. 3A-C, once the first and second pattern ends 34, 36 are joined so as to create a tubular structure, the leaflet portion 50 can then be folded about the fold line 52 and inverted into the interior of the skirt portion 40. As such, the leaflet portion 50 of the valve body 30 sits within and generally abutting the skirt portion 40.

With continued reference to FIGS. 3A-C, once folded so that the leaflet portion 50 is within the skirt portion 40, the leaflet and skirt portions 50, 40 are attached to one another. More specifically, the first and second leaflet edges 64, 66 are attached to the respective first and second window side edges 72, 74 of corresponding leaflet supports 80. As shown, the edges 64, 66, 72, 74 preferably generally align so as to be conducive to being connected by a seam. Further, the commissural tabs 60 are attached to the downstream ring 76 of the skirt portion 40. Preferably, such attachments are accomplished through stitching in a conventional manner using conventional materials such as suture material. However, other materials, such as adhesives, may also be used. Additionally, in some embodiments, the commissural tabs can be secured to the skirt by a clip in lieu of or in addition to a stitching. Also, in still further embodiments, the leaflet and skirt portions can be formed separately and then connected at, for example, an upstream ring. Such an alternative will apply to other embodiments and features discussed herein.

Once the leaflet portion 50 has been appropriately connected to the skirt portion 40, the valve body 30 can move between the open condition depicted in FIG. 3A to the closed condition depicted in FIGS. 3B and 3C. As shown in FIGS. 3B and 3C, when closed, the valve leaflets 54 coapt with one another so as to block blood from flowing upstream between the leaflets 54. Also, since the leaflets 54 are sewn securely onto the skirt 40 at the supports 80, no blood will flow between the skirt portion 40 and leaflet portion 50 at the upstream end 78 of the valve body 30, thus preventing paravalvular leaks. In the illustrated embodiment, the windows 70 of the skirt portion 40 generally align with the leaflets 54. As such, when the leaflets 54 are in the closed condition, blood flow is deflected by the leaflets 54 and readily flows through the windows 70.

The valve body 30 of FIGS. 3A-C is appropriate to use to replace a patient's native valve and embodiments employing features described in connection with the illustrated valve body 30 can be used alone or in conjunction with a stent frame. For example, in one embodiment, a valve body 30 as in FIG. 3A can be installed into the annulus of a patient's native aortic valve. In such an embodiment, the upstream ring 78 is sewn or otherwise attached to the native valve annulus, and the downstream ring 76 is attached to the aorta downstream of the annulus. As such, the valve body 30 sits in the aortic sinus. In this embodiment, the windows 70 of the skirt portion 40 are particularly useful in that when the leaflets 54 coapt, blood readily flows through the windows 70 and into the cardiac arteries that branch off of the aortic sinus.

Figures 4A, 4B:
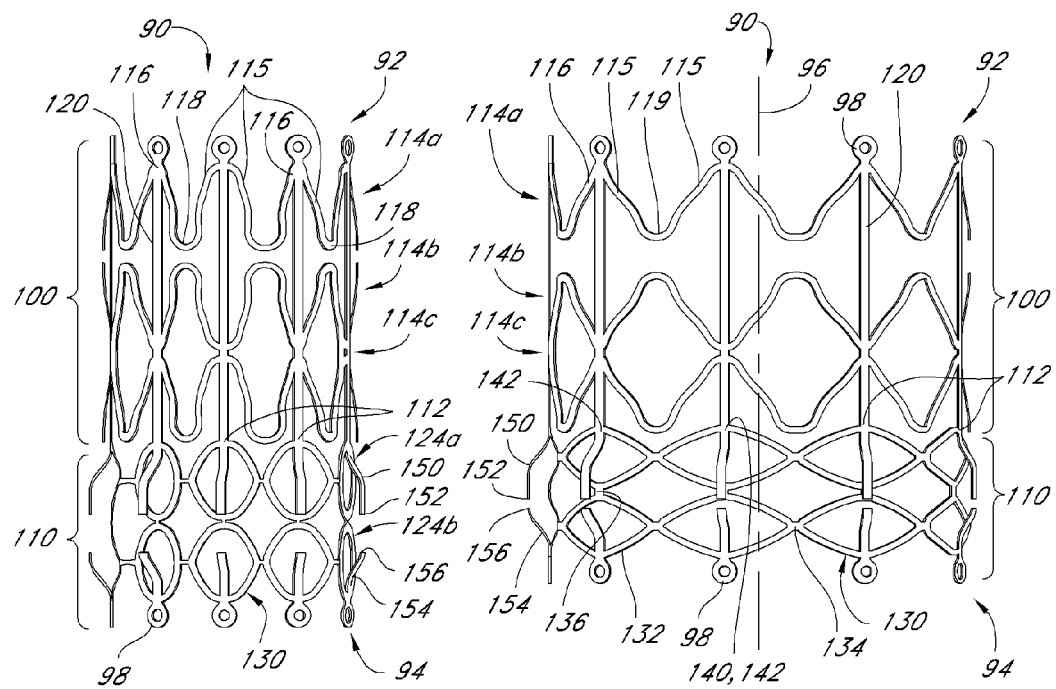
FIG. 4A is a schematic view of an embodiment of a stent frame, shown in a compacted state.
FIG. 4B shows the stent frame of FIG. 4A in an expanded state.
Figure 5:
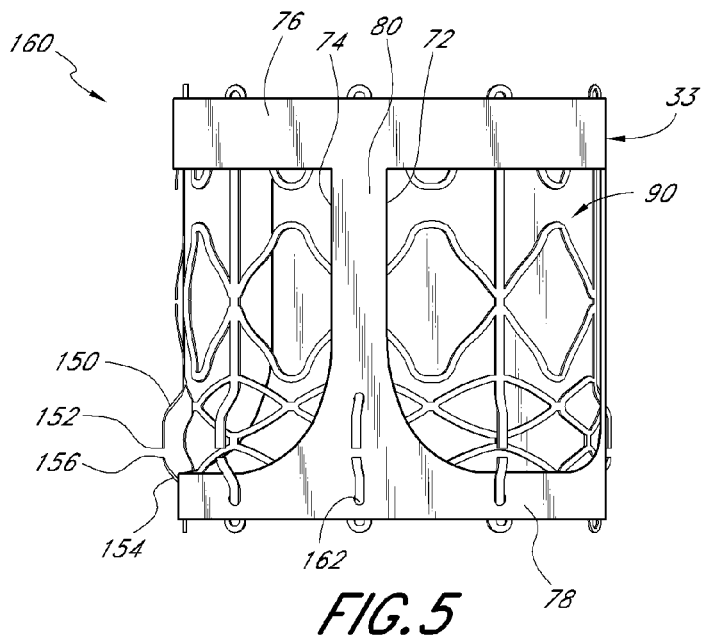
FIG. 5 is a side view of the stent frame of FIGS. 4A and B with the valve body of FIGS. 1-3 mounted thereon.

With reference next to FIGS. 4 and 5, a heart valve body 30 as in FIG. 3 can be mounted onto a stent 90. Such a stent can be of various designs and characteristics. For example, such a stent may be self-expandable, balloon-expandable, a hybrid, or the like.

With particular reference to FIGS. 4A and 4B, the illustrated stent frame 90 embodiment supports the valve body 30 and can be expanded from a compacted state as shown in FIG. 4A to an expanded state as shown in FIG. 4B. The illustrated stent 90 preferably is a self-expanding stent constructed of a flexible material, preferably a shape memory material such as nitinol. As it is self-expanding, the stent 90 is in a fully opened state, as depicted in FIG. 4B, when relaxed. The illustrated stent 90 preferably is elongate from a first end 92 to a second end 94 and is tubular with a longitudinal axis 96 and a generally circular cross section. It is to be understood that in other embodiments stents can have a non-circular cross section, such as a D-shape, an oval or an otherwise ovoid cross-sectional shape. In the illustrated embodiment a plurality of spaced apart eyelets 98 are provided both at the first end 92 and at the second end 94 of the stent frame 90. Other embodiments may be constructed without such eyelets 98.

The illustrated stent frame 90 has a non-foreshortening portion 100 and a foreshortening portion 110. The portions are joined at a transition 112 between the first and second ends 92, 94. Foreshortening refers to a behavior in which the length of the stent 90 in the foreshortening portion 110 decreases as the radius of the stent increases from the compacted state to the expanded, deployed state. As such, in FIG. 4A, which shows the stent frame 90 in a compacted state, the foreshortening portion 110 of the stent frame 90 is longer than when the stent is in the expanded state illustrated in FIG. 4B.

With continued reference to FIG. 4B, the non-foreshortening portion 100 of the illustrated stent 90 comprises a plurality of rows or rings 114*a-c* of circumferentially expansible elements, or struts 115, arranged in a zigzag pattern. The struts 115 are configured to expand and contract with a change in radius of the stent 90. In the illustrated embodiment, the stent has three such rings 114*a-c*. It is to be understood that more or fewer rings can be employed as desired to accomplish the purposes of this stent frame. In the illustrated embodiment, the respective ends of each circumferential undulating strut 115 joins an adjacent strut 115 at an apex 116, 118 which is, in at least some embodiments, an area of preferential bending. In the illustrated embodiment, the zigzag pattern of a first 114*a* and a third ring 114*c* are generally in phase with one another, while the struts 115 of a second ring 114*b* between the first and third rings 114*a*, 114*b* are generally out of phase with those of the first and third rings. It is to be understood that, in other embodiments, all or most of the rings can be in phase with one another or out of phase as desired.

With continued reference to FIG. 4B, longitudinal struts 120 extend transversely across the rings 114*a-c* of the non-foreshortening portion 100 from the first end 92 of the frame 90 to the transition 112. More particularly, each ring 114 shares a common longitudinal strut 120. The longitudinal struts 120 extend through apices 116 of adjacent rings 114, and preferably extend the entire length of the non-foreshortening portion 100. Preferably, the longitudinal struts 120 comprise a non-expandable rod or bar. The apices 116 that are connected to the longitudinal struts 120 are referred to as "connected" apices 116. Apices 118 not connected to longitudinal struts 120 are referred to as "free" apices 118.

As noted above, the longitudinal struts 120 are not substantially expandable in a longitudinal direction. As such, even though the undulating struts 115 provide flexibility in radial expansion or compaction, as the stent 90 changes radial size between the compacted and expanded states, the longitudinal length of the stent in the non-foreshortening portion 100 remains substantially unchanged. In other embodiments, the longitudinal struts may include expansible elements that may allow the struts to expand somewhat longitudinally. However, such longitudinal expansion would not be directly tied to any change in strut radius.

With continued reference to FIGS. 4A and 4B, the foreshortening portion 110 of the illustrated stent frame comprises a first and a second circumferential ring 124*a*, 124*a* that are each made up of interconnected cells 130. Each cell 130 comprises a plurality of strut members 132 that are interconnected in such a way that when the stent expands radially, the cell 130 becomes longitudinally shorter. In the illustrated embodiment, each cell 130 is enclosed and is configured in generally a diamond-shaped pattern. Circumferential and longitudinal cell connectors 134, 136 connect adjacent cells 130 to one another. An upper end 140 of each cell 130 in the first ring 124*a* is connected to a second end 142 of a corresponding longitudinal strut 120 of the non-foreshortening portion 100 at the transition 112.

Although the illustrated foreshortening cells 130 are arranged in a diamond pattern, it is to be understood that other configurations can be employed. For example, in other embodiments, the foreshortening cells can be generally oval-shaped, and in further embodiments the cells may not be fully enclosed. As discussed above and illustrated in FIGS. 4A and 4B, when the illustrated stent 90 is expanded from the compacted state to the expanded state, the non-foreshortening portion 100 of the stent remains substantially the same length while the foreshortening portion 110 of the stent becomes substantially shorter in length.

With continued reference to FIGS. 4A and 4B, a plurality of first anchors 150 extend from the transition 112 into the foreshortening portion 110. Preferably, each of the anchors 150 also extends generally radially outwardly from the stent 90 so that a tip 152 of each first anchor 150 is spaced from the cells 130. Similarly, a plurality of second anchors 154 extend from the foreshortening cells 130 at or adjacent the second end 94 of the stent frame 90 and extend into the foreshortening portion and radially outwardly from the stent so that a tip 156 of each second anchor 154 is spaced from the cells 130. A first distance is defined between the tips 152, 156 of opposing first and second anchors 150, 154 when the stent 90 is in the compacted state, and a second distance is defined between the tips 152, 156 of opposing first and second anchors 150, 154 when the stent 90 is in the expanded state. As shown, the second distance is substantially less than the first distance. This arrangement enables the foreshortening portion 110, with its anchors 150, 154, to grasp onto tissues so as to hold the stent in place.

In preferred embodiments, the stent 90 may be deployed into a heart valve annulus, and positioned when compacted so that the tips 152, 156 of the opposing first and second anchors 150, 154 are disposed on opposite sides of the native annulus. As the stent is expanded, the opposing first and second anchors are drawn closer together so as to grasp opposite sides of the native annulus and securely hold the stent in position. As such, the stent can be held securely in position without requiring a substantial radial force against the native annulus. Applicant's U.S. patent application Ser. No. 12/084,586, which was published on Aug. 27, 2009 as U.S. Publication No. 2009/0216314, discusses embodiments of foreshortening stents with anchors, and can be referred to for further discussion of certain aspects of the illustrated stent embodiment. The discussion in the above application concerning structure and operation of embodiments of a foreshortening stent, particularly a foreshortening stent having anchors, is expressly incorporated by reference herein.

In the illustrated embodiment, the stent is made of a shape-memory alloy, specifically nitinol. It is to be understood, however, that other materials, including metals, metal alloys and non-metals can be employed as appropriate.

In a preferred embodiment, the stent frame is initially provided as a circular cross-section nitinol tube. The tube is laser cut according to a pattern corresponding to the struts, cells and the like. The cut tube preferably is electrochemically polished to as to remove rough edges. The cut and polished nitinol tube may be shaped in accordance with a desired manner, such as shaping the anchors to extend radially outwardly, and the nitinol stent frame may be heated-treated to both establish the shape memory and to obtain desired elasticity attributes.

With specific reference next to FIG. 5, an embodiment of a replacement heart valve 160 is illustrated in which the valve body 30 of FIGS. 1-3 is disposed on the stent frame 90 of FIG. 4. In this embodiment, the skirt portion 40 of the valve body 30 is disposed on the outside of the stent 90 and the leaflet portion 50 is disposed on the inside of the stent 90. The downstream ring 76 and leaflet supports 80 are attached to the stent 90. Apertures 162 are formed through the skirt 40 as appropriate to accommodate the anchors 150, 154. The anchors 150, 154 and corresponding apertures 162 are configured so that when the stent 90 is compacted, the anchors still extend through the apertures. More specifically, when the stent 90 is compacted and the foreshortening portion 110 lengthens, the anchors 150, 154 move within the corresponding apertures 162, but the anchor tips 152, 156 do not exit the apertures 162.

In one embodiment, during manufacture, the skirt portion 40 is attached to the stent 90 before any portion of the leaflet portion 50 is attached to the skirt portion 40. In some embodiments, the skirt portion 40 is fit over the stent 90 prior to folding the leaflet portion 40. In other embodiments, the stent is slid between the leaflet portion and skirt portion after they are folded. After the stent 90 is sandwiched between the leaflet portion 50 and skirt portion 40, the leaflets 54 are attached to the leaflet supports 80 and the commissural tabs 60 are attached to the downstream ring 76. In some embodiments, such attachments are made such that at least portions of the valve body can move relative to the stent while the stent is foreshortening.

In another embodiment, the skirt portion 40 of the valve body 30 is attached to the outside of the stent 90, and the stent and valve body are compressed into the compacted state without the leaflet portion 50 being folded relative to the skirt portion 40. As such, the leaflet portion 50 is not in contact with or directly connected to the stent 50. During a procedure to deploy the replacement valve into a patient, the partially-completed assembly is advanced into place and the stent is expanded so that the anchors grasp the patient's native annulus. The leaflet portion 50 of the valve is then folded over and into the stent 90, and is then attached, while in place, to the skirt portion 40.

Figure 6A:
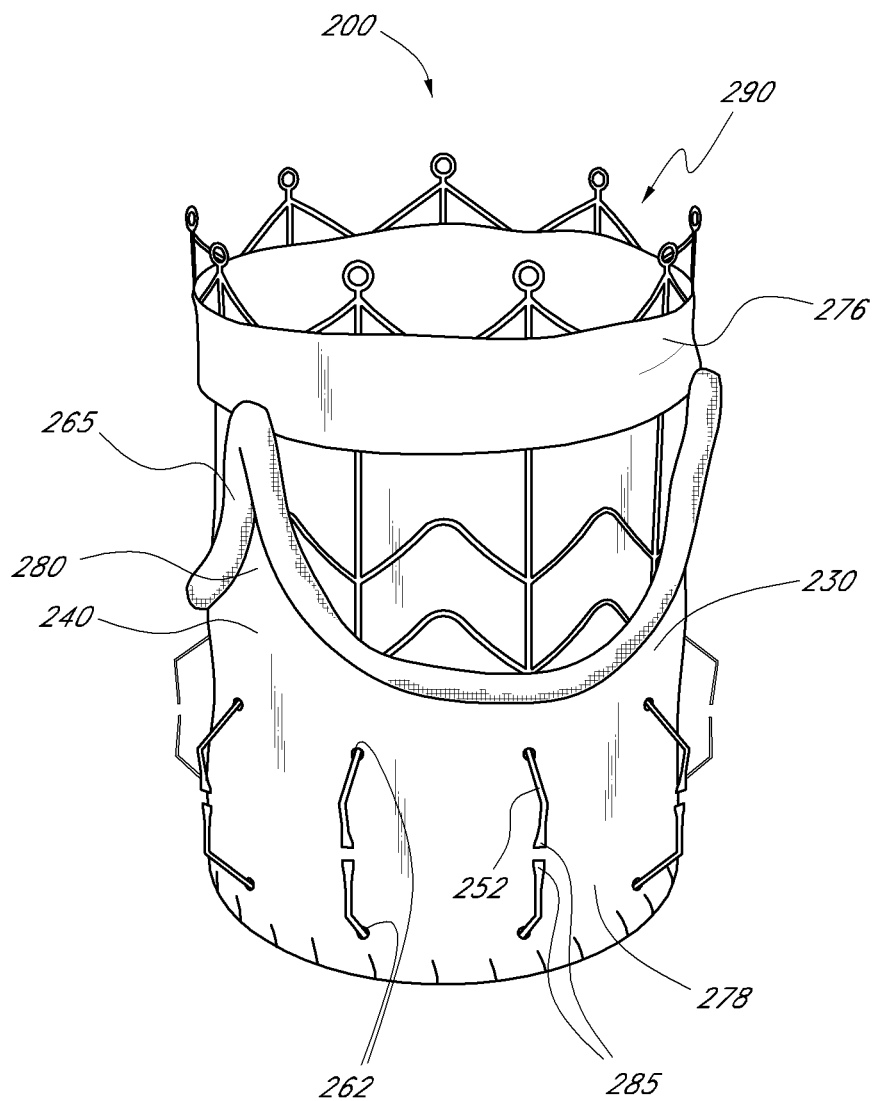
FIG. 6A is a side perspective view of another embodiment of a heart valve comprising a tissue valve body mounted on a stent frame.
Figure 6B:
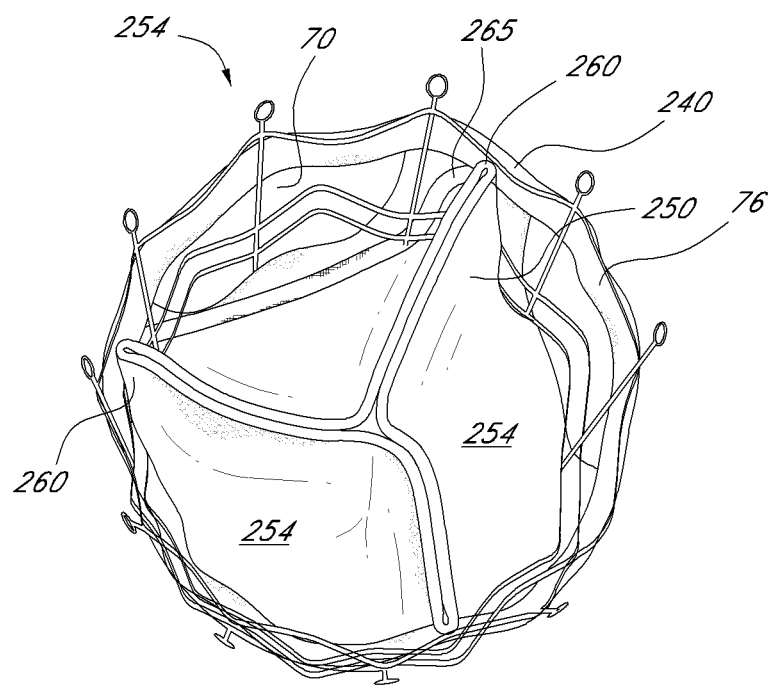
FIG. 6B shows the heart valve of FIG. 6A in a closed condition and viewed from a downstream position.
Figure 6C:
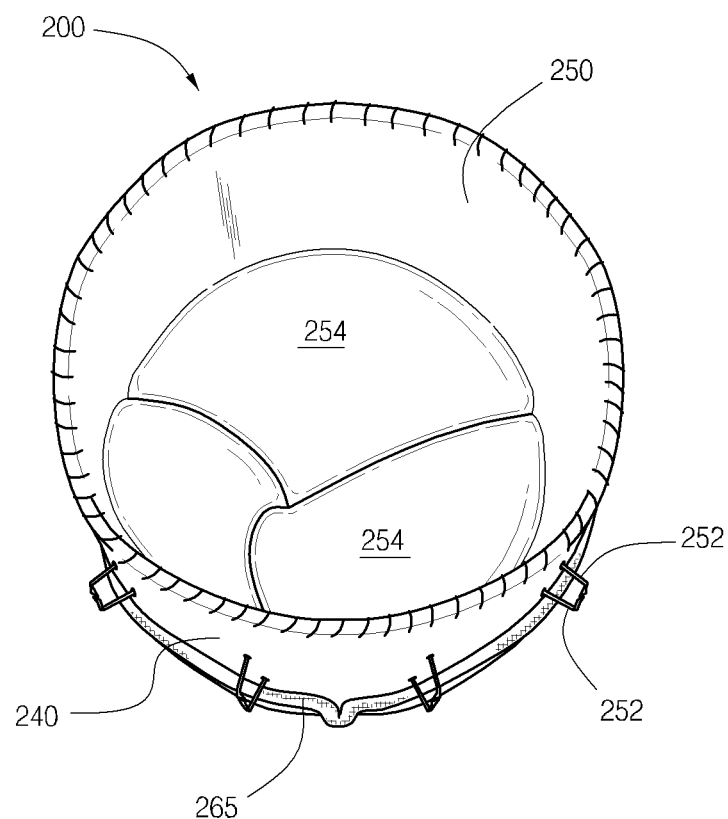
FIG. 6C shows the heart valve of FIG. 6A in a closed condition and viewed from an upstream position.

With reference next to FIGS. 6A-C, another embodiment of a heart valve 200 is illustrated in which a stent frame 290 is sandwiched between an inner layer 250 and an outer layer 240 of a valve body 230. In preferred embodiments the valve body 230 is formed of a single piece of tissue wrapped about the stent frame 290 so that the skirt portion 240 is the outer layer and sits on and is attached to the outside of the stent 290. The leaflet portion 250 is the inner layer. It sits within the interior of the stent 290 and is attached to the skirt portion 240. In the illustrated embodiment, first and second side edges 264, 266 of leaflets 254 are tightly sutured to first and second side edges 272, 274, respectively, of leaflet support portions 280. Commissural tabs 260 of the leaflet portion 250 are attached to a downstream ring 276 of the skirt portion 240. In this arrangement, the connection between the leaflet portion 250 and the skirt portion 240 securely holds onto the stent 290, but also prevents leaks. Further, the downstream ring 276, to which the commissural tabs 260 are attached, helps to distribute forces exerted on the commissural tabs during valve closure.

Stent anchors 250, 254 in the embodiment illustrated in FIGS. 6A-C extend through aperture 262 in an upstream ring 278 of the valve body 230. In the illustrated embodiment, the stent anchors 250, 254 have a widened portion 285 towards their tips 252, 256. As such, during elongation of a foreshortening portion 210 of the stent 290 in which the anchors 250, 254 are drawn apart from each other, the enlarged portions 285 of the anchors help prevent the tissue valve body 230 from slipping off the anchors or, more specifically, prevent the anchor tips 252, 256 from slipping through their associated apertures 262.

In additional embodiments, a valve body 230, 30 as depicted in FIGS. 6A-C or as in FIGS. 1-4 can be mounted to a stent frame that does not foreshorten upon expansion. As in embodiments above, the skirt 40, 240 can be disposed on the outside of the stent frame, and the leaflet portion 50, 250 is inverted and folded so as to be within the stent frame, but aligned with the skirt portion. The leaflet portion and skirt portion are then sewn together as appropriate so that at least part of the stent frame is sandwiched between the portions. Preferably the valve body material is contiguous at the fold line between the skirt portion and leaflet portion, which is at or adjacent to the upstream end of the heart valve, thus further decreasing the likelihood of paravalvular leaks.

Figure 7:
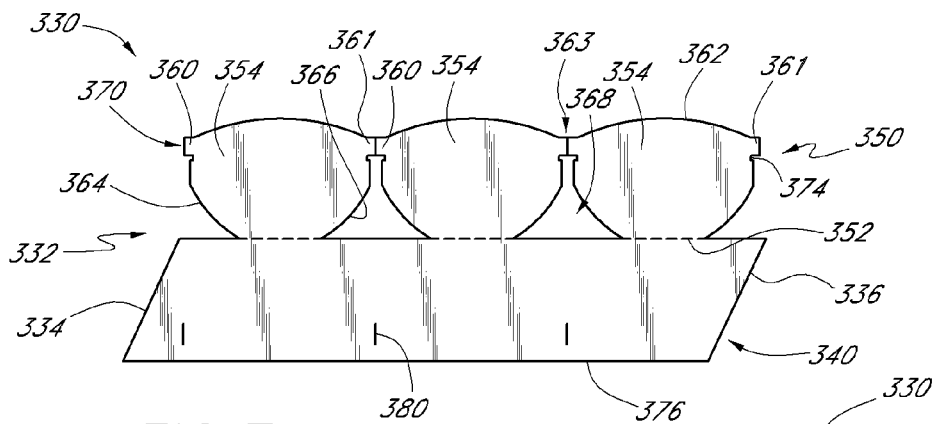
FIG. 7 shows a flat pattern for cutting a flat source tissue to form another embodiment of a valve body.

With reference next to FIGS. 7-9A, another embodiment of a valve body 330 is depicted. FIG. 7 discloses a flat pattern 332 for cutting flat source tissue to assemble into the valve body embodiment. The illustrated valve body pattern 332 has first and second ends 334, 336, and defines a skirt portion 340 and a leaflet portion 350. The leaflet portion 350 comprises three leaflets 354, each having a downstream leaflet edge 362 and opposing first and second leaflet side edges 364, 366. An aperture 368 is cut between adjacent leaflets 354 and the cut out tissue removed so as to define the leaflets 354.

Each of the leaflets 354 has a first and a second opposing commissural tab portion 360, 361. In the illustrated flat pattern 332, the commissural tab portions 360, 361 of adjacent leaflets 354 are initially co-formed as a connection 363 between adjacent leaflets. During cutting according to the flat pattern, this commissural connection 363 between adjacent leaflets 354 is cut so as to define the first and second commissural tabs 360, 361 of adjacent leaflets, which first and second commissural tabs 360, 361 have first and second cut ends 370, 371, respectively. In the illustrated embodiment, a relatively small jog, or offset 374, is cut between each leaflet side edge 364, 366 and the adjacent commissural tab 360, 361.

With continued reference to FIG. 7, preferably the skirt portion 340 of the valve body 330 is substantially contiguous, without significant cut-outs such as the windows of the FIG. 1-4 valve body. The skirt 340 has a downstream edge 376, and is connected to the leaflet portion 350 at a fold line 352. In the skirt portion 340, the valve pattern's first and second ends 334, 336 are cut to be diagonal relative to the downstream edge 376, which preferably is parallel to the fold line 352. In the illustrated embodiment, commissural slits 380 are cut into the skirt portion 340 so as to be generally aligned with the cut edges 370, 371 of adjacent first and second commissural tabs 360, 361.

Figure 8:
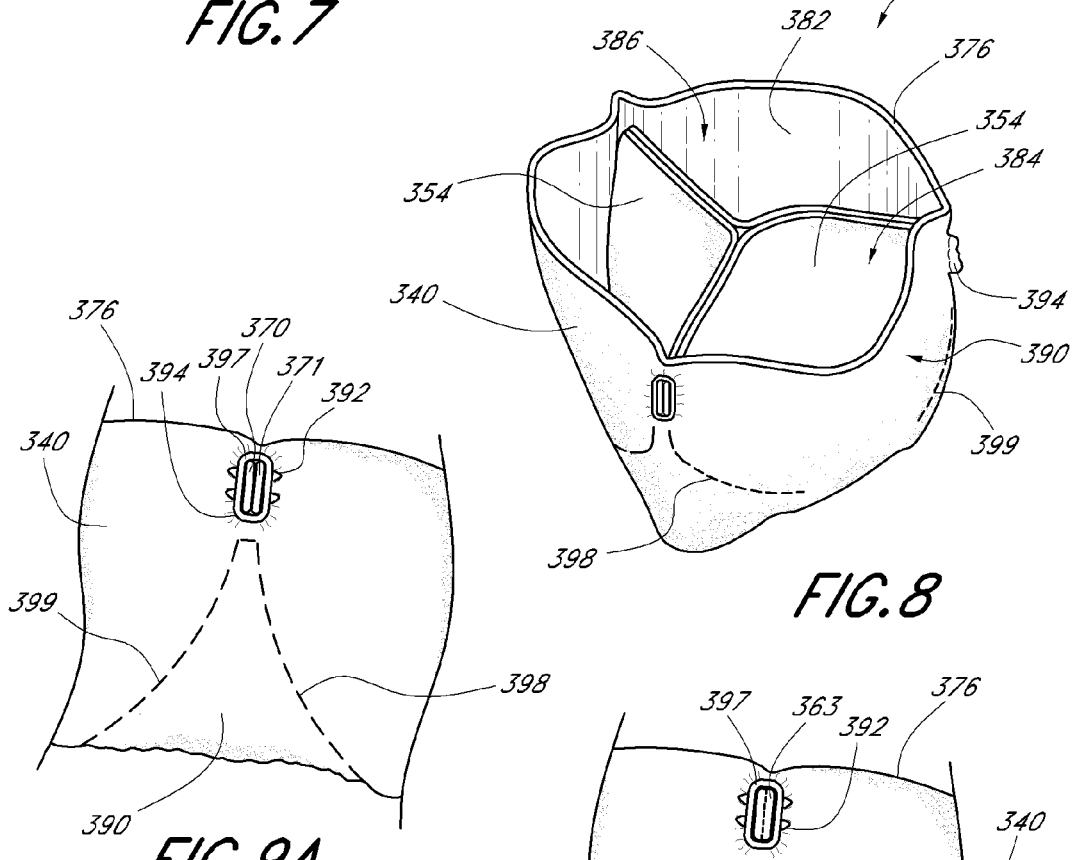
FIG. 8 shows a perspective view of a valve body constructed of tissue cut according to the pattern of FIG. 7.

With specific reference next to FIG. 8, the valve body 330 is constructed by folding the skirt portion 340 relative to the leaflet portion 350 along the fold line 352, and securing the diagonal ends 334, 336 of the skirt portion 340 together to establish the tubular shape of the valve body 330. In this arrangement, an inner surface 382 of the skirt portion 340 faces outer surfaces 384 of the leaflets 354, and an interior 386 of the valve body 330 is defined by the inner surface 382 of the skirt portion 340. Inner surfaces of the first and second commissural tab portions 360, 361 of adjacent leaflets 354 are engaged with one another, and the engaged tabs 360, 361 are passed through the corresponding commissural slit 380 of the skirt portion 340. With specific reference also to FIG. 9A, which is a close-up view taken from outside the skirt portion, the engaged first and second commissural tab portions 360, 361 are arranged so that their cut ends 370, 371 are facing generally radially outwardly and are adjacent the outer surface 390 of the skirt portion 340.

The engaged commissural tab portions 360, 361 are connected to one another, preferably by sutures 392. In the illustrated embodiment, a slit edge portion 394 immediately surrounding the slit 380 is made to engage the outer surfaces 396 of the commissural tabs 360, 361 so that a cut edge 397 of the slit 380 faces radially outwardly as do the cut ends 370, 371 of the tabs 360, 361. The slit edge portion 394 and engaged commissural tabs 360, 361 then are all sewn together as shown in FIG. 9A.

In the illustrated embodiment, the inner surface 382 of the skirt 340 in the slit edge portion 394 engages an outer surface of the tabs 360, 361. In still other embodiments, the engaged commissural tabs 360, 361 are first sewn-together on the outside of the skirt 340, and the sewn-together commissural tabs 360, 361 are then sewn onto the tissue surrounding the slit 380. In another embodiment, the engaged commissural tabs 360, 361 are not sewn to one another. Instead, each tab is folded adjacent its cut edge 370, 371 to engage the outer surface 390 of the skirt portion 340 adjacent the slit 380, and is then sewn to the skirt. In another such embodiment the engaged portion of the commissural tabs 360, 361 can also be sewn together, or held together by clips or the like.

Figure 9A:
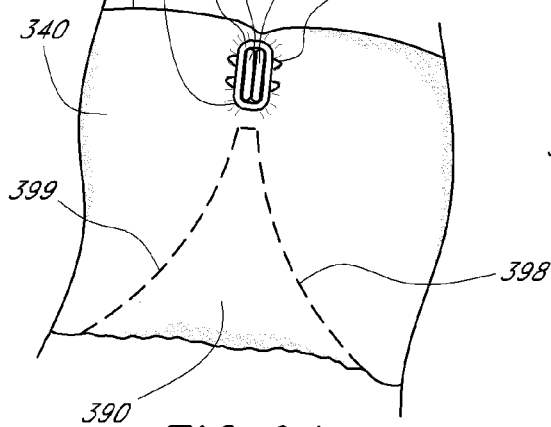
FIG. 9A is a close-up view of a side of the valve body of FIG. 8.
Figure 9B:
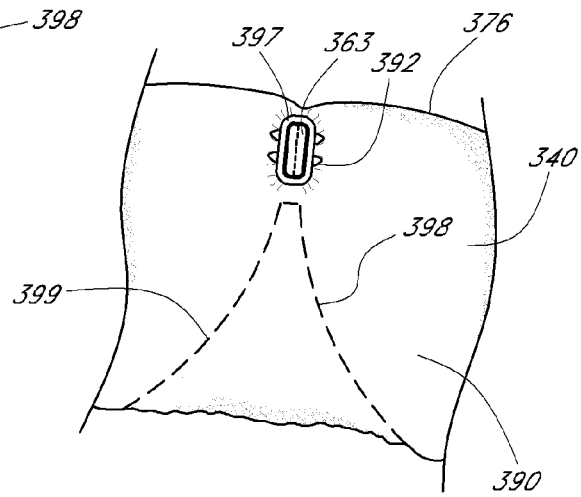
FIG. 9B is a close-up view as in FIG. 9B but showing features of another embodiment.

With continued reference to FIGS. 7-9A, the first and second leaflet side edges 364, 366 are also sewn to the skirt portion 340. As such, a good seal is sewn between the leaflets 354 and the skirt portion 340 so as to prevent any blood leakage therebetween during operation of the valve. FIGS. 9A and B show first and second seams 398, 399 that attach the leaflets 354 to the skirt along the first and second leaflet side edges 364, 366.

The offset 374 between the leaflet side edges 364, 366 and the tabs 360, 361 facilitates a clean transition between the tabs, which extend through the commissural slit 380, and the leaflet side edges, which are sewn to the inner surface 382 of the skirt portion 340. Preferably the leaflet edge in the offset 374 also engages the skirt.

The valve body 330 can be sewn together in several ways. In another embodiment, the commissural slits 380 can be used as a guide during folding of the leaflet portion 350 over the skirt portion 340, and the operator is careful to make sure the leaflets 391 are properly aligned. In another embodiment, prior to forming the valve body into a tube, but after folding, at least one and preferably at least two of the leaflets 354 are sewn onto the skirt 340. Sewing the leaflets onto the skirt when still in a flattened state can be more convenient. This method also enables reliable placement of the leaflets 354 in the correct position relative to the skirt 340, and maintenance of them in a correct placement during suturing. Also, since at least one of the leaflets is already sewn securely in place before the valve body 330 is formed into a tube by connecting the first and second skirt ends 334, 336, the previously-connected leaflet or leaflets function as a guide and reference point to assist in proper placement and sewing of the remaining leaflet(s).

Of course, in other embodiments, the valve body 330 can be rolled into a tube prior to folding and/or prior to attaching the leaflets 350 to the skirt portion 340. For example, in one embodiment the commissural tabs 360, 361 are attached and put in place once the valve body 330 is rolled into a tube. Once secured in place, the tabs 360, 361 serve as a guide to help maintain the leaflets 354 in a correct position while they are attached to the skirt 340.

In another embodiment, a valve body 330 is provided having a structure substantially as in the valve body of FIGS. 7 and 8, except that the commissural connection 363 between adjacent leaflets 354, which in FIG. 7 is cut to form opposing commissural tabs 360, 361, is not cut, but instead remains as a commissural tab 363 connecting adjacent leaflets 354. Such an embodiment can be constructed substantially as described above; however, only the commissural tabs 360, 361 at the first and second pattern ends 334, 336 have cut edges 370, 371 so as to be constructed as shown in Figure A.

With specific reference to FIG. 9, in an embodiment having a contiguous commissural tab 363 between the leaflets 354, each tab 363 preferably is folded so that inner surfaces of the tab 363 are engaged. The folded tab 363 is passed through the corresponding commissural slit 380. Each folded commissural tab 363 is sutured to the skirt portion 340, preferably in a manner similar to the embodiments discussed above.

Figure 10:
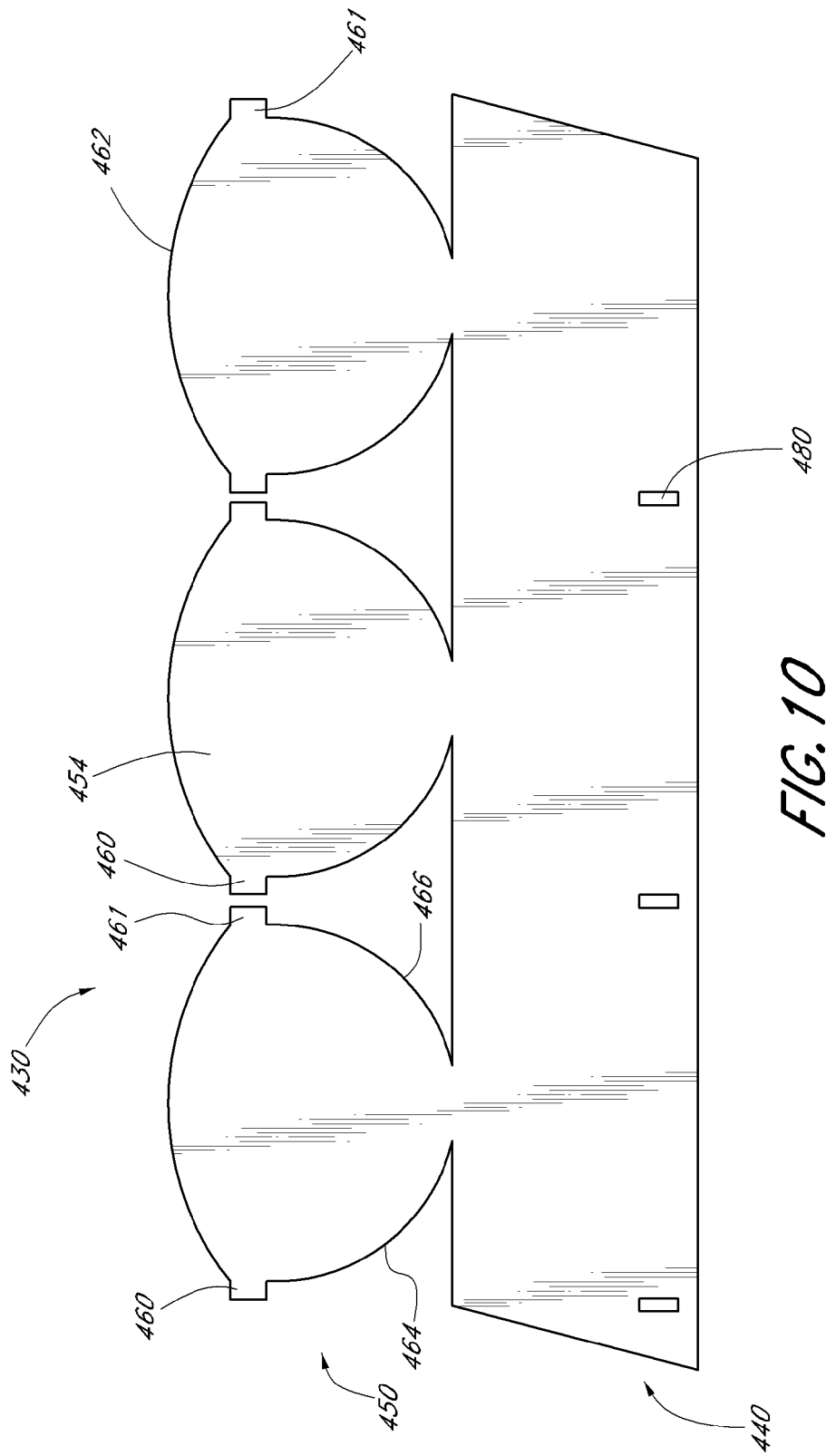
FIG. 10 shows a flat pattern for cutting a flat source tissue to form yet another embodiment of a heart valve body.

With reference next to FIG. 10, another embodiment of a flat pattern 432 for cutting a valve body 430 from a flat source tissue is illustrated. In this embodiment, the valve body 430 is divided into a skirt portion 440 and a leaflet portion 450. The leaflet portion 450 comprises three leaflets 454, each having a curved downstream leaflet edge 462 and curved first and second side edges 464, 466. Opposing first and second commissural tab portions 460, 461 are also defined on each leaflet 454. In the illustrated pattern, the commissural tab portions 460, 461 and side edges 464, 466 are formed by removing tissue between the leaflets 454, including between adjacent first and second tab portions of adjacent leaflets. Three commissural slots 480 are cut through the skirt portion 440 generally corresponding to the placement of the commissural tabs 460, 461. The slots 480 of the illustrated embodiment are formed by cutting and removing a portion of tissue, as opposed to simply cutting a slit as in some other embodiments. Once cut from source tissue, the valve body 430 can be constructed in a manner sharing similarities with the valve body 330 of FIGS. 7-9.

Figure 11:
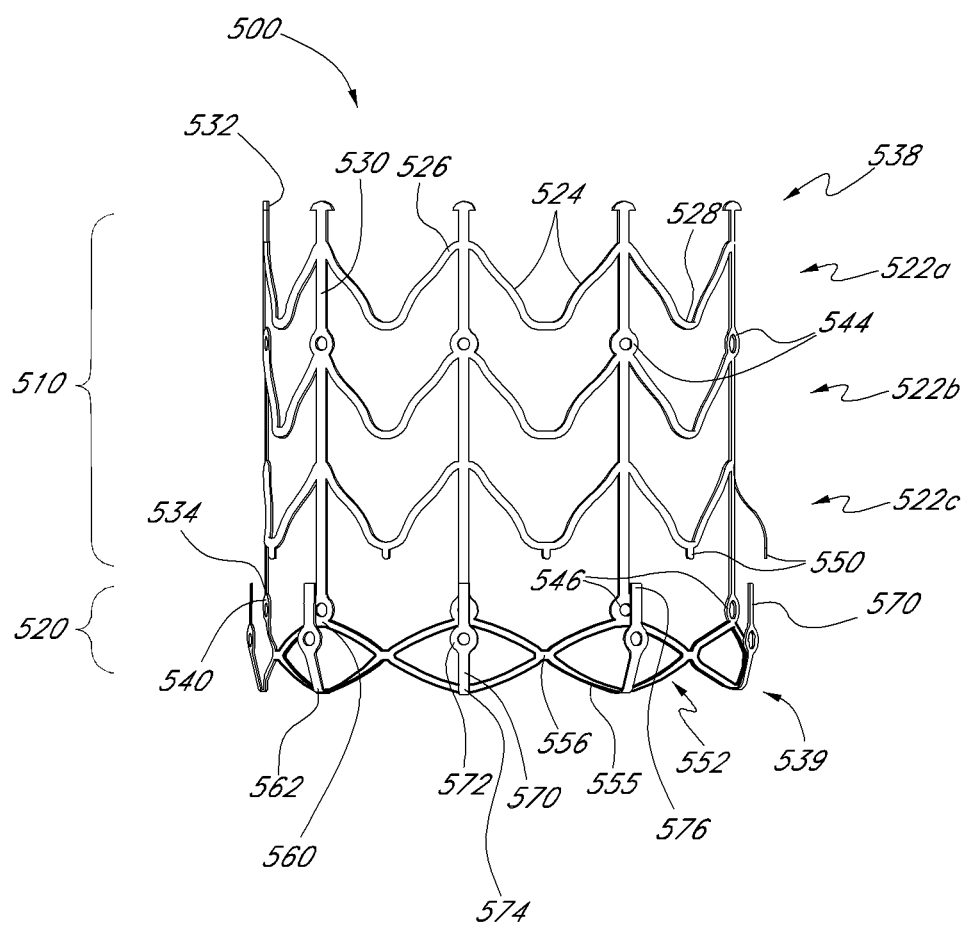
FIG. 11 is a schematic side view of another embodiment of a stent frame for supporting a heart valve body.

With reference next to FIG. 11, another embodiment of a stent frame 500 is illustrated. In the illustrated embodiment, the stent frame 500 comprises a non-foreshortening portion 510 and a foreshortening portion 520. The non-foreshortening portion 510 comprises three rings 522a-522c of undulating circumferentially expansible struts 524 that connect to one another at apices 526, 528. Longitudinal struts 530 have first and second ends 532, 534, and extend from a first end 538 toward a second end 539 of the stent 500 but terminate at a transition 540 from the non-foreshortening portion 510 to the foreshortening portion 520. The apices that intersect with the longitudinal struts 530 are referred to as "connected" apices 526, and apices between connected apices 526 are referred to as "free" apices 528.

In the illustrated embodiment, a first ring 522a is disposed adjacent the first end 538 of the stent and a second ring 522b is disposed adjacent the first ring 522a. A set of first eyelets 544 are formed at the connected apices 526 of the second ring 522b. A set of second eyelets 546 are also formed at the second ends 534 of each longitudinal strut 530, which in the illustrated embodiment is also the transition 540. In a third ring 522c, the free apices 528 each comprise a protuberance 550 extending therefrom, which protuberance can also be referred to as an apical anchor 550. Preferably the struts 524 in the third ring 522c are pre-shaped so as to flare radially outwardly when the stent frame 500 is in an expanded state as shown in FIG. 11.

With continued reference to FIG. 11, the foreshortening portion 520 of the illustrated stent frame 500 comprises a ring 552 of generally diamond-shaped cells 555 connected to one another at connectors 556. A first end 560 of each cell 555 is connected to the non-foreshortening portion 510 at the second eyelets 546. As in embodiments discussed above, the foreshortening cells 555 are configured so that as the stent frame 500 is radially compacted, the foreshortening portion 520 of the stent becomes longitudinally longer and, correspondingly, when the stent frame is expanded radially, the foreshortening portion 520 shortens.

A second end 562 of each cell 555 in the foreshortening portion 520 is attached to an anchor 570 that extends generally radially outwardly and toward the first end 538 of the stent. An anchor eyelet 572 is formed in each anchor 570, preferably between a base 574 and a tip 576 of each anchor 570. During operation, and consistent with other embodiments discussed herein, as the stent 500 in a compacted state is placed at a native heart valve annulus, the compacted stent is first arranged so that the annulus is disposed between the apical anchors 550 and the anchor tips 576. The stent 500 is then allowed to expand, prompting foreshortening, which brings the anchor tips 576 closer to the apical anchors 500 and grasps the native annulus therebetween. In the illustrated embodiment, the apical anchors 500 are not collinearly aligned with the end anchors 570.

Figure 12:
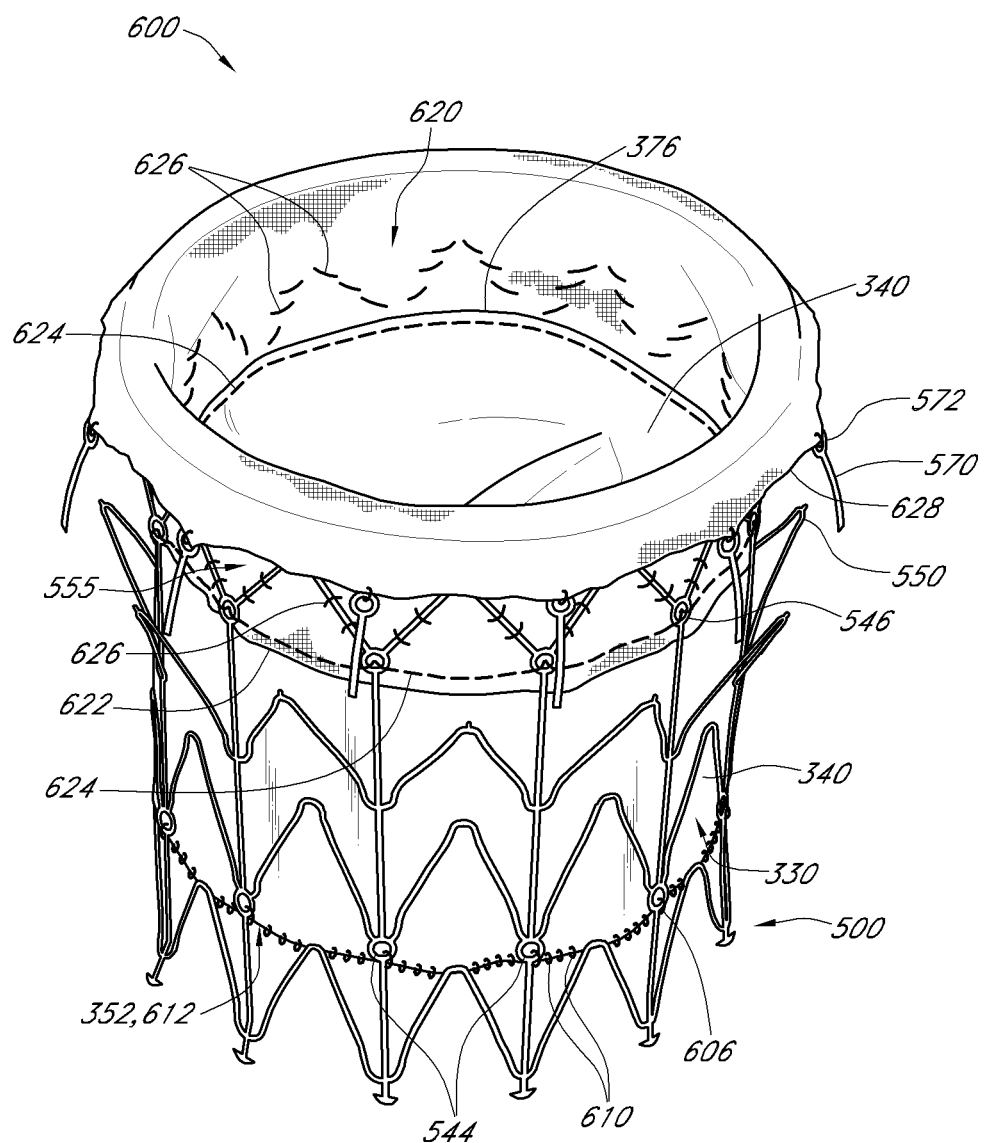
FIG. 12 is a perspective view of the stent frame of FIG. 11 with a heart valve body constructed from source tissue cut in accordance with the pattern of FIG. 10 mounted thereon.
Figure 13:
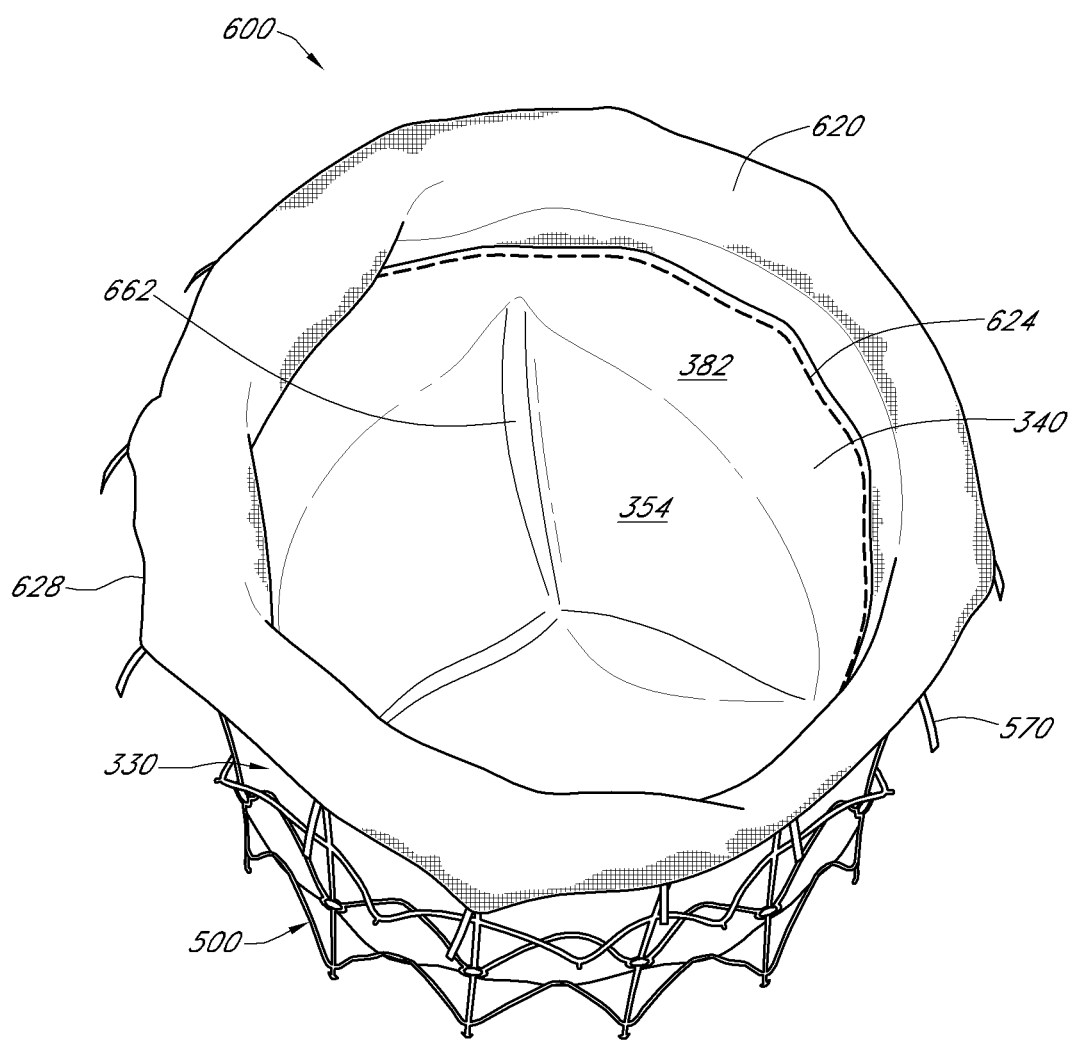
FIG. 13 shows the heart valve of FIG. 12 in a closed condition and viewed from a downstream position.

With additionally reference to FIGS. 12 and 13, an embodiment of a replacement heart valve 600 comprises a valve body 330 as in FIGS. 7-9 attached to a stent frame 500 as in FIG. 11. In this embodiment, however, the entire valve body 330 is disposed inside the stent 500. More specifically, and as illustrated in FIG. 12, the skirt portion 340 of the valve body 330 is sewn to the first eyelets 544 of the stent. In the illustrated embodiment, the fold line 352 of the valve body 330 is hemmed, and certain stitches 606 of a hem seam 610 also engage the first eyelets 544 in the non-foreshortening portion 510 of the stent 500. In this illustrated embodiment, the hemmed fold line 352 becomes an upstream end 612 of the valve body 330.

With continued reference to FIGS. 12 and 13, an elongate tubular portion 620 of flexible, longitudinally expandable fabric is attached to the downstream end 376 of the skirt portion 340 in the illustrated embodiment. More particularly, a first end of the fabric 622 is sewn to the downstream end 376 of the skirt portion about the circumference of the skirt portion by a downstream seam 624. Also, the fabric 620 preferably is connected to the outer surface of the skirt 340, and is also sewn onto the second eyelets 546 of the stent frame 500. Preferably, the fabric 620 is also sewn to the foreshortening cells 555 at several points by connector stitches 626.

In the illustrated embodiment, the fabric 620 curves around the second end 539 of the stent frame 500, generally following the curvature of the downstream anchors 570. Second end 628 of the fabric portion 620 is sewn to the anchor eyelets 572. Preferably, the flexible fabric 620 is sufficiently expandable to move with the foreshortening portion 520 as the stent 500 moves between the compacted state and the deployed, relaxed expanded state. As such, in the illustrated embodiment, the tissue valve body 330 is confined to the non-foreshortening portion 510 of the stent and the flexible fabric 620 spans the foreshortening portion 520 of the stent. Thus, the tissue valve body 330 is not subject to longitudinal expansion and contraction with the stent 500.

In the illustrated embodiment, the tissue portion of the valve body 330 is sewn directly to the stent frame 500 at only the upstream end 612. The downstream edge 376 of the skirt portion 340 is attached to the fabric 620, which fabric is sewn directly to the stent 500 at the second eyelets 546 via the downstream seam 624. In another embodiment, the same seam 624 that connects the fabric 620 to the skirt 340 also connects the skirt 340 to the second eyelets 546.

With continued reference to FIGS. 7-9 and 11-13, the illustrated embodiment of an assembled heart valve 600 comprises two layers of tissue, preferably formed from a single, contiguous piece of tissue. The leaflet portion 350 of the valve, which includes the leaflets 354, is sewn directly only to the skirt portion 340. As such, during valve operation between open and closed states, the leaflet portion 350, and specifically the leaflets 354, directly engages only the skirt portion 340. In turn, the skirt portion 340 is attached to and interacts with the stent 500 and other materials such as the downstream fabric portion 620.

It is to be understood that, in other embodiments, a portion or all of what has been shown as the fabric portion 620 in the embodiment illustrated in FIGS. 12 and 13 can be replaced by providing a longer skirt portion of the tissue valve portion. It is also to be understood that, in additional embodiments, the illustrated valve body 330 can be used with a non-foreshortening stent.

Figure 14:
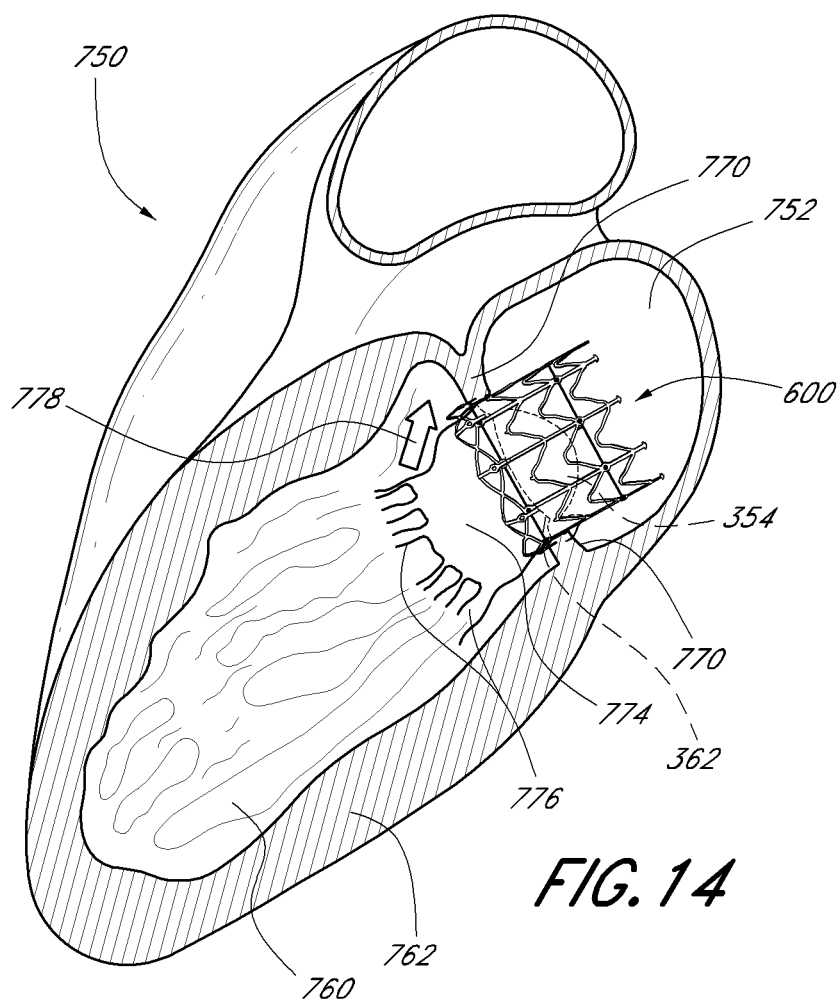
FIG. 14 shows the heart valve of FIG. 12 placed in a mitral annulus of a human heart in accordance with one embodiment.

With reference next to FIG. 14, a schematic representation of the heart valve 600 as discussed above in connection with FIGS. 12 and 13 is depicted installed in a human heart 750. The heart is shown in cross-section, and represents typical anatomy, including a left atrium 752 and left ventricle 760. The left ventricle 760 is defined by a muscular wall 762. The left atrium 752 and left ventricle 760 communicate with one another through a mitral annulus 770. Also shown schematically in FIG. 14 is a native anterior mitral leaflet 774 having chordae tendinae 776 that connect a downstream end of the anterior mitral leaflet 774 to the muscle wall 762 of the left ventricle 760. A left ventricle outflow tract 778 extends toward the top of the left ventricle 760.

As shown in FIG. 14, the valve 600 of FIGS. 12-13 is disposed so that the mitral annulus 770 is grasped between the anchors 570 and apical anchors 550 in accordance with a method of aligning and deployment of the stent 500 discussed previously. As such, all or most of the stent 500 extends into the left atrium. The portion of the stent 500 disposed upstream of the annulus 770 can be referred to as being positioned supra-annularly. The portion generally within the annulus 770 is referred to as positioned intra-annularly. The portion downstream of the annulus is referred to as being positioned sub-annularly. In the illustrated embodiment, only a part of the foreshortening portion is positioned intra-annularly or sub-annularly, and the rest of the stent 500 is supra-annular.

In the illustrated embodiment, the anterior mitral leaflet 774 has not been removed prior to deploying the replacement valve 600. Preferably, the posterior mitral leaflet (not shown) also has not been removed prior to deploying the replacement valve. However, in other embodiments, one or both of these natural valve leaflets may be removed before deploying the replacement valve.

With the stent 500 placed mostly supra-annularly within the left atrium 752, the stent 500 does not interfere with left ventricle function during pumping. More specifically, the stent 500 does not interfere with blood flow from the left ventricle 760 through the outflow tract 778 and does not interfere with deformation of the left ventricle 760 as the muscle wall 762 contracts during pumping. In the illustrated embodiment, the valve body 330 is attached to the stent 500 so that the downstream edges 362 of the valve are generally within the mitral annulus 770. This is referred to as intra-annular placement of the valve body 330.

Figure 15:
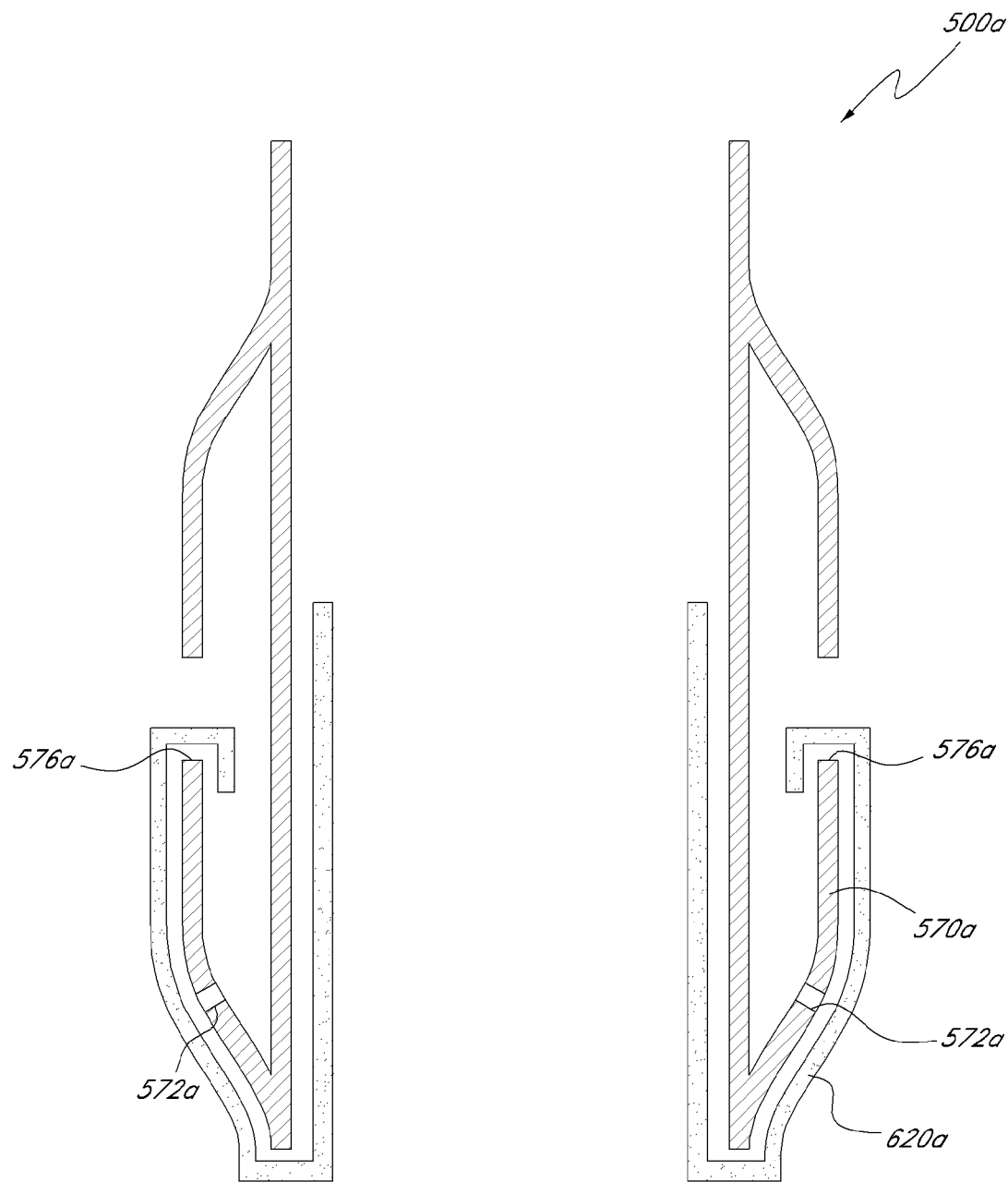
FIG. 15 is a schematic side section view showing opposing walls of a heart valve stent frame similar to that of FIG. 11 and schematically showing placement of an expandable fabric portion on the stent in accordance with another embodiment.

With reference next to FIG. 15, a schematic cross-sectional side view schematically showing a portion of a stent 500a and fabric portion 620a of another embodiment. This embodiment is similar to that of FIGS. 12 and 13, except that the fabric portion 620a extends beyond anchor eyelets 572a and up to anchor tips 576a. Preferably the fabric 620a is wrapped about the anchor tips 576a and secured in place with a seam around the circumference of the fabric 620a so as to form a generally contiguous band at the tips 576a of the anchors 570a. As such, each anchor 570a will contact the native valve annulus through the fabric 620a.

Figure 16A:
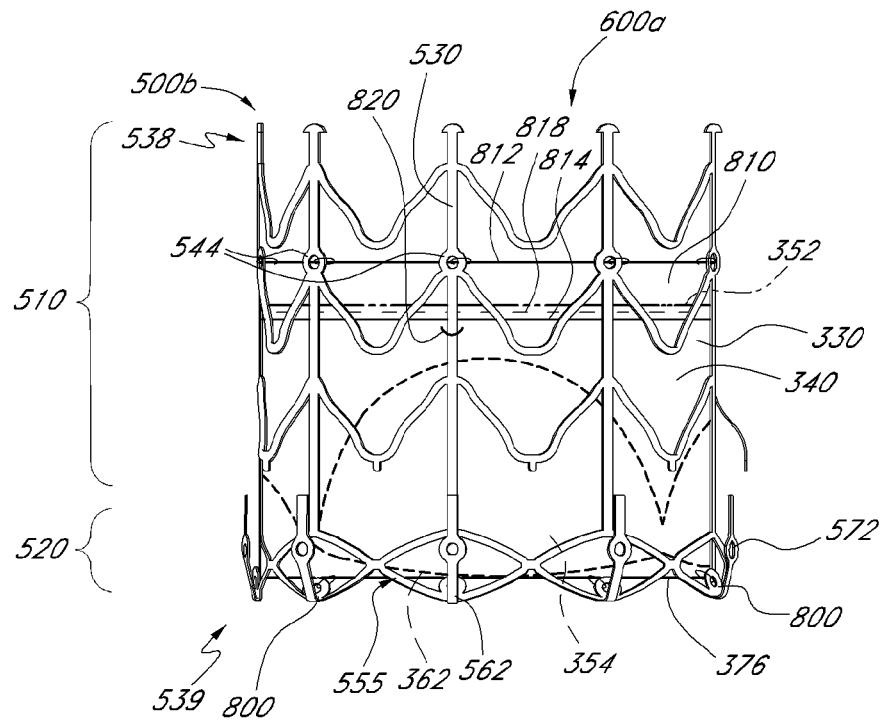
FIG. 16A is a side view of another embodiment of a heart valve, showing the valve body of FIG. 8 mounted onto a stent in accordance with another embodiment.

With reference to FIG. 16A, another embodiment of a heart valve 600a is shown. The illustrated heart valve 600a employs a valve body 330 as discussed above in connection with FIGS. 7-9 mounted on a stent 500b that, for demonstration purposes, is mostly similar to the stent 500 of FIGS. 11-13. As indicated in FIG. 16A, stent 500b, being almost the same as stent 500, includes most of the same structure and uses the same reference numbers. Such structure is described in connection with the discussion of stent 500 above.

In the illustrated stent 500b, a plurality of distal eyelets 800 are provided at the downstream end 539 of the stent 500b, which is also the second end 562 of cells 555 in the foreshortening portion 520 of the stent 500b. In this embodiment, the valve body 330 is attached to the stent 500b so that the downstream edge 376 of the skirt portion 340 is connected to the downstream eyelets 800, such as by sutures. As such, the leaflets 354, and particularly the downstream edges 362 of the leaflets 354, are arranged at, adjacent, or in some embodiments downstream of, second end 539 of the stent 500b.

With continued reference to FIG. 16A, an elongate tubular flexible portion 810, having opposing first and second ends 812, 814, is attached to the valve body 330. More specifically, the second end 814 of the flexible portion 810 is attached to the upstream end 352 of the skirt 340, preferably with a circumferential stitch 818. The first end 812 of the flexible portion 810 is attached to the stent 500b at the first eyelets 544. Preferably, the upstream end 352 of the valve body 330 is not directly attached to the stent 500b, but is only attached to the flexible portion 810, which in turn is attached to the stent 500b.

Preferably the flexible portion 810 is constructed of a flexible material that can increase and decrease in length as the length of the stent 500b increases and decreases due to foreshortening during radial compaction and expansion. Also, preferably the valve body 330 is constructed of a material such as pericardium, which is flexible yet not substantially longitudinally stretchable. To the extent the valve body is made with a material that stretches, preferably the flexible portion 810 is more amenable to longitudinal stretching than the valve body 330 so that as the length of the stent 500b increases, the flexible portion 810, rather than the valve body 330, will stretch longitudinally, and vice versa.

Figure 16B:
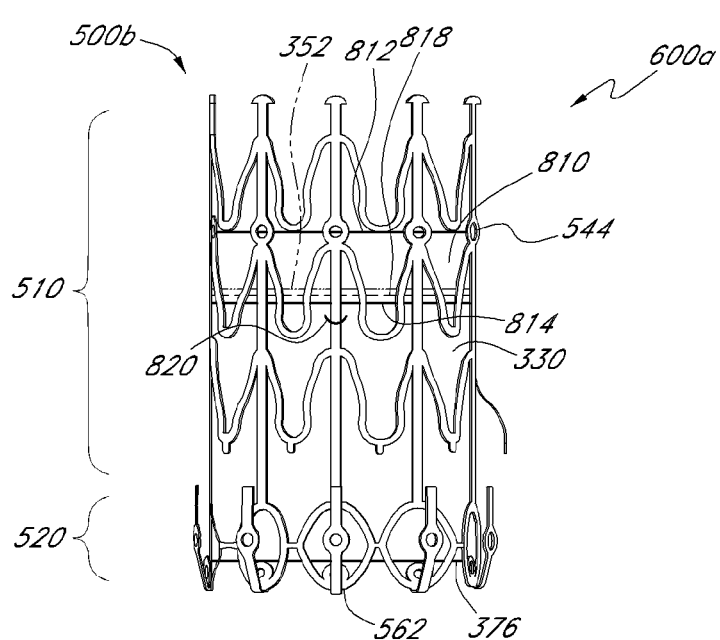
FIG. 16B is a side view of the assembly of FIG. 16A shown in a compacted state.

With additional reference to FIG. 16B, it is noted that in the illustrated embodiment, a portion of the valve body 330 spans the foreshortening portion 520 of the stent. The longitudinally stretchable flexible portion 810, however, is disposed in the non-foreshortening portion 510 of the stent 500b. As the assembled valve 600a is compacted from the expanded portion shown in FIG. 16A to the compacted state shown in FIG. 16B, the foreshortening portion 500 becomes longer. Since the valve body 330 does not stretch substantially, and instead the flexible portion 810 stretches substantially during such lengthening, the stent 500b moves longitudinally relative to the valve body 330. Such a "floating valve body" configuration enables placement of the valve body over at least a portion of the foreshortening portion 520 of the stent 500b without stretching the valve body during lengthening of the foreshortening portion of the valve during the compaction and expansion process.

In the embodiment illustrated in FIGS. 16A and B, at least part of the skirt 340, preferably at or adjacent the upstream end, is loosely attached to one or more longitudinal struts 530 of the stent 500b in a manner that accommodates the floating, longitudinal movement of the valve body 330 relative to the stent 500b upon compaction and expansion, such as by one or more loose stitches 820. In other embodiments, such loose stitches 820 can be in the flexible portion adjacent the valve body. Preferably the stitches 820 are relatively loose so that as the stent 500b moves between the compacted and expanded states, each stitch 820 slides longitudinally over the corresponding longitudinal strut 530. Such stitches 820 are strategically placed so that there is an undisturbed path for the stitch to slide upon.

In the illustrated embodiment, the flexible portion 810 is constructed of a fabric having a sufficiently loose weave and/or material that accommodates longitudinal stretching during compaction, and also takes up the slack as the stent shortens during expansion. It is to be understood, however, that other types of materials and configurations can be employed for the flexible portion. For example, in another embodiment, an elongate tubular portion of pericardium makes up the flexible portion. In this embodiment, preferably the pericardium is creased so as to preferentially fold, accordion style, as the stent shortens during expansion. In another embodiment, the flexible portion comprises a pericardium segment having several fenestrations, which are strategically placed slits that, upon application of longitudinal tension to the pericardium, deform so as to enable the pericardium segment to stretch longitudinally. However, as the stent is expanded and foreshortens, the pericardium recovers to its original shape. After the valve is deployed, and as time passes, tissue in-growth will help to close the fenestrations. In still other embodiments, yet additional structures can be employed. For example, rather than a tubular flexible portion, the flexible portion can comprise an array of elastic cords that attach to the upstream end of the valve body 330, extend longitudinally upon compaction of the valve, and take up the slack as the valve is expanded. Also, although the illustrated embodiment employed the valve body 330, which has two layers, it is to be understood that other embodiments may employ a single-layer valve connected to a flexible portion and mounted on a stent having a foreshortening portion.

Figure 17:
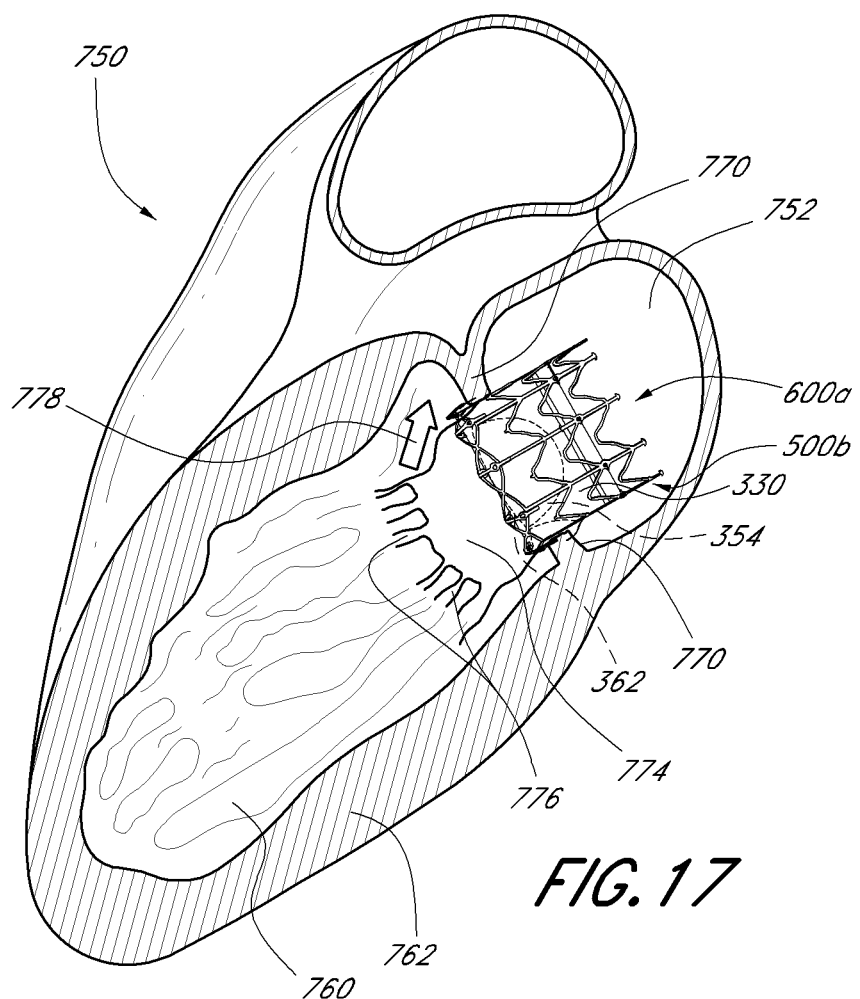
FIG. 17 shows the heart valve of FIG. 16 placed in a mitral annulus of a human heart in accordance with another embodiment.

With reference next to FIG. 17, a schematic representation is made of the valve 600a of FIGS. 16A and B mounted in a human heart. In the illustrated embodiment, the stent 500b is mounted in a manner substantially similar to the stent 500 depicted in FIG. 14. However, the valve body 330 is positioned farther downstream relative to the stent so that the leaflets 354 are generally within the mitral annulus 770, which position can be referred to as intra-annular or partially intra-annular, as the downstream edges 362 of the leaflets 354 may be downstream of the annulus, and thus sub-annular. It is to be understood that, in other embodiments, a valve body can be mounted relative to the stent to be entirely supra-annular, intra-annular, sub-annular, or combinations thereof.

Figure 18:
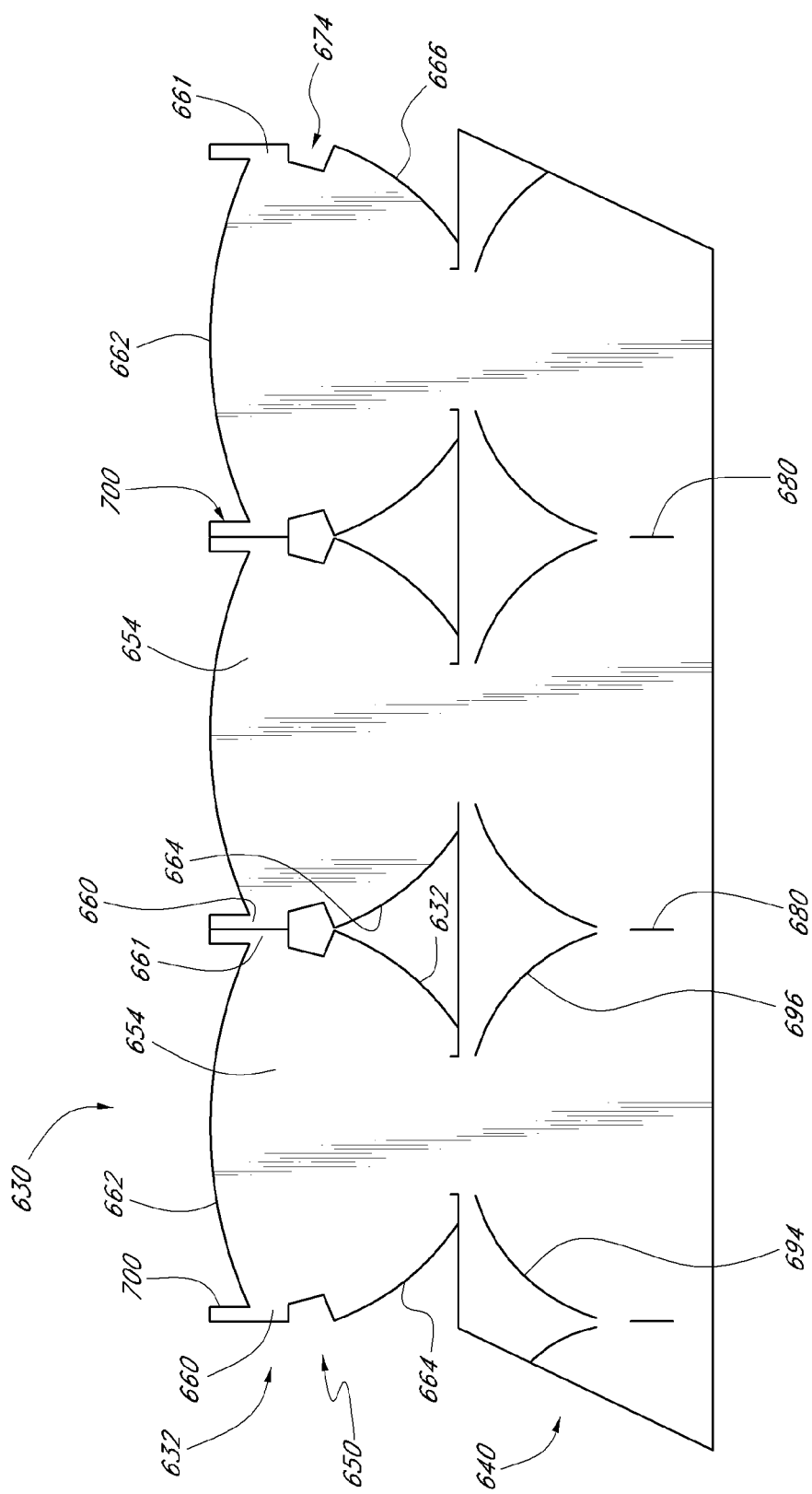
FIG. 18 shows a flat pattern for cutting a flat source tissue to form yet another embodiment of a valve body.
Figure 19:
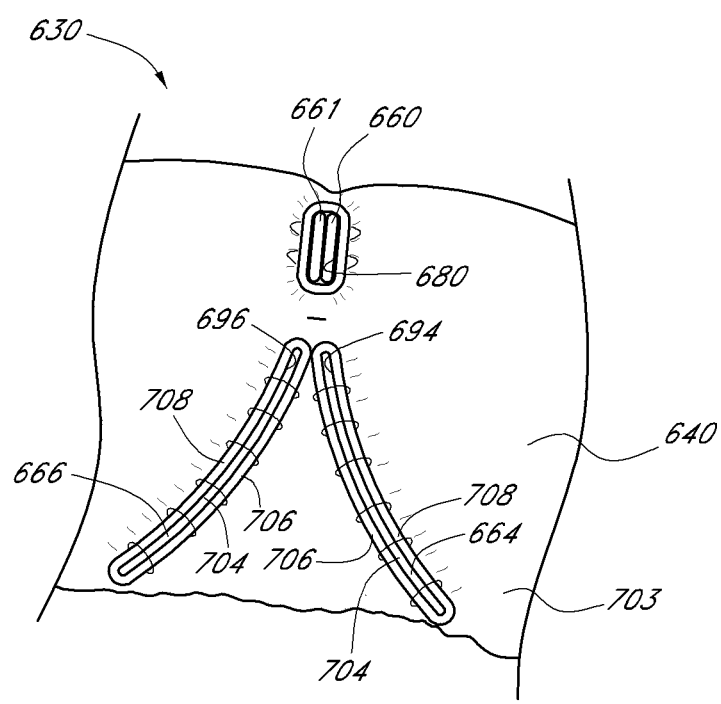
FIG. 19 depicts a perspective view of a heart valve body constructed from the pattern of FIG. 18.

With reference next to FIGS. 18 and 19, yet another embodiment of a valve body 630 is illustrated. FIG. 18 shows a flat pattern 632 for cutting the valve body 630 out of flat source tissue. As shown, the pattern 632 comprises a skirt portion 640 and a leaflet portion 650. The leaflet portion 640 comprises three leaflets 654 each having a downstream edge 662 and opposing first and second side edges 664, 666. Each leaflet 654 has opposing first and second commissural tab portions 660, 661. An offset 674 is provided between each leaflet side edge 664, 666 and the adjacent commissural tab 660, 661.

In the skirt portion 640, three commissural slits 680 are cut so as to generally align with the commissural tabs 660, 661. First and second leaflet edge slits 694, 696 are also cut in the skirt portion 640 so as to generally align with the curvature of the corresponding first and second leaflet side edges 664, 666. In the illustrated embodiment, a portion 700 of each commissural tab 660, 661 extends in the downstream direction beyond at least a portion of the leaflet downstream edge 662.

With continued reference to FIGS. 18 and 19, to construct the valve body 630 from flat tissue cut according to this pattern 632, the cut tissue is folded and the first and second leaflet edges 664, 666 are pushed through corresponding first and second leaflet slits 694, 696, respectively. Edges of the skirt portion 640 at and adjacent the leaflet slits 694, 696 preferably are deformed so that the inner surface of the skirt 640 at and adjacent the slits 694, 696 engages inner and outer surfaces of the leaflet 654 so that a leaflet cut end 704 and opposing slit cut ends 706, 708 face radially outwardly. The leaflet cut end 704 and slit cut ends 706, 708 are then sutured together. As such, the sutures connecting the leaflet edges 664, 666 to the skirt 640 are maintained generally on the outside 703 of the skirt portion 640, and portions of the leaflets 654 within the valve body 630 generally do not engage the sutures during use. Similarly, and in the manner as discussed in other embodiments, the first and second commissural tab portions 660, 661 of adjacent leaflets 654 are arranged to engage one another face-to-face, extended through the slit 680, and sewn to each other and the skirt 640 at the slit edge.

In still other embodiments, the leaflet side edges 664, 666 can be extended through corresponding slits 694, 696, folded to engage with the outer surface 703 of the skirt portion 640, and then sutured into place.

In the illustrated embodiment, the downstream portion 700 of the commissural tab portions 660, 661 contributes to surface area for sewing the commissural tab portions in place and provides material to hold onto during the manufacturing process. In some embodiments, the entire commissural tab 660, 661 is sewn to the skirt 640. In other embodiments, a portion of the tabs are sewn in place, and an unused remainder of each tab is removed and discarded.

Figure 20:
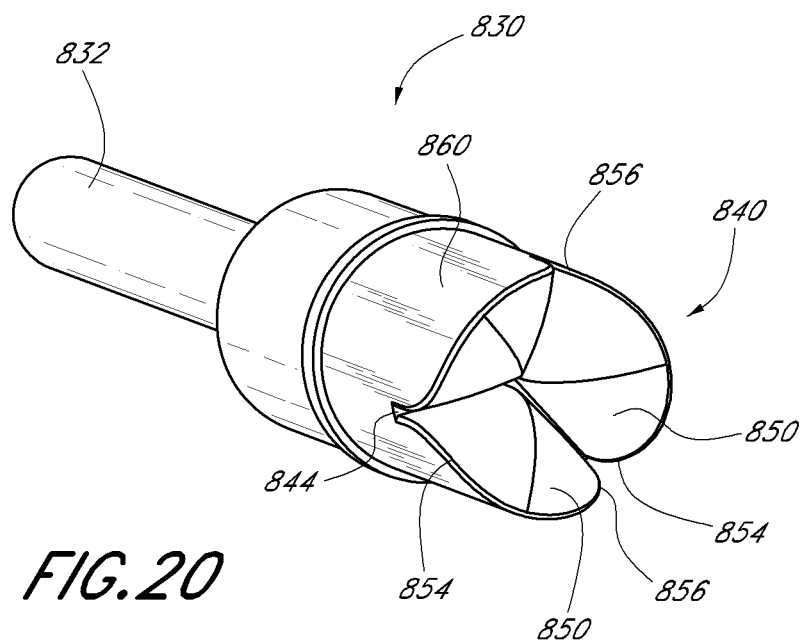
FIG. 20 is a perspective view of an embodiment of a tool for constructing a tissue valve body.

With reference next to FIG. 20, a tool 830 for helping to construct the valve body 630 of FIGS. 18 and 19 is illustrated. The tool 830 has a proximal handle portion 832 and a form 840, or mold, at its distal end. Preferably, the form 840 is shaped to be the negative of a desired shape of the downstream portion of the valve body 630 when the leaflets 654 are coapted in a closed position. The illustrated form 840 comprises a stop surface 844 and a plurality of leaflet engagement surfaces 850, each of which have first and second side edges 854, 856.

Figure 21:
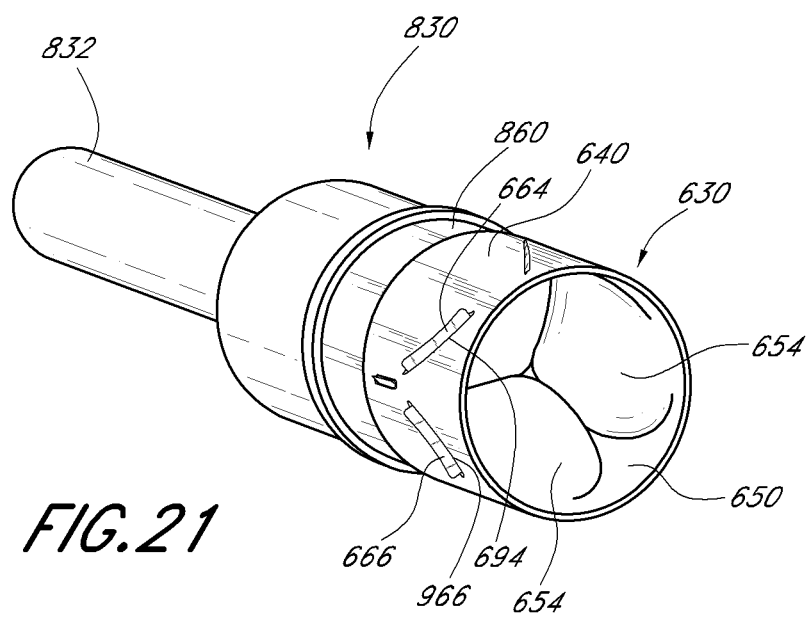
FIG. 21 shows the tool of FIG. 20 being used to construct a tissue valve body as in FIG. 18-19.
Figure 22:
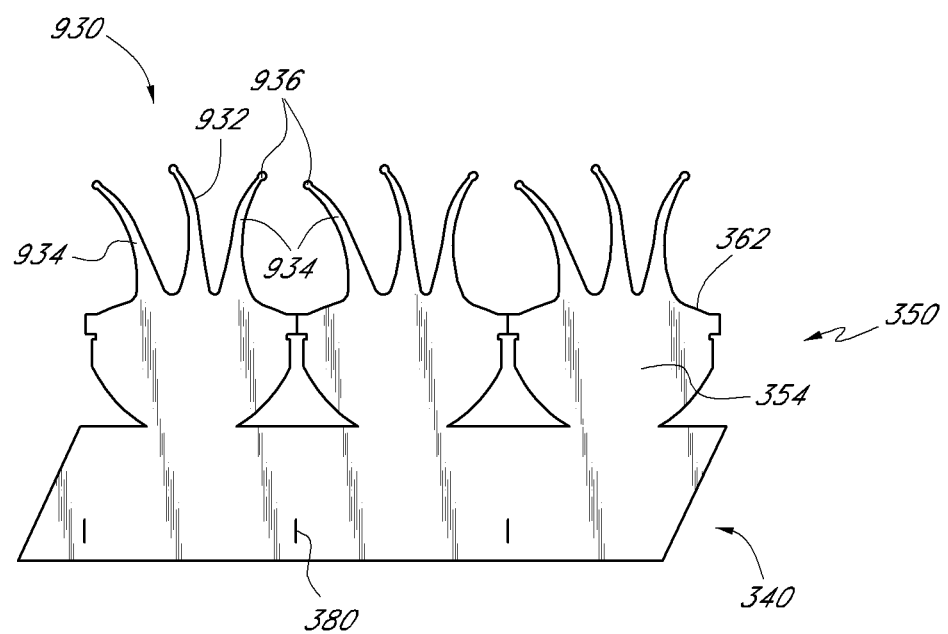
FIG. 22 shows a flat pattern for cutting a flat source tissue to form another embodiment of a valve body.

With additional reference to FIG. 21, the tool 830 is shown during construction of a valve body 630. In a preferred embodiment, the valve body 630 is cut according to the pattern 632 discussed above, and is then formed into a tube and connected at the commissural tabs 660, 661. Preferably, the commissural tabs 660, 661 are initially only tacked in place, and thus serve as a guide for placement of the partially assembled valve body 630 on the form 840. The downstream end of the partially assembled valve body 630, is then placed upon the form 840 so that the skirt 640 engages a circumferential outer surface 860 of the form, and the leaflets 654 engage corresponding leaflet engagement surfaces 850 and the first and second side edges 664, 666 of the leaflets 654 are generally aligned with the first and second side edges 854, 856 of the leaflet engagement surfaces 850. Preferably, downstream edges 662 of the leaflets 654 are at or adjacent the stop surface 844 of the form 850.

In a preferred embodiment, the operator correctly positions the valve body 630 on the form 840 and pulls side edges 664, 666 of the leaflets 654 through the corresponding leaflet slits 694, 696 of the skirt portion 640, all of which are preferably aligned with the leaflet engagement surface side edges 854, 856. In this manner, the partially-assembled valve body 630 becomes engaged with the form 840, taking on the form's shape so that the leaflets are configured in the preferred coapted position. As such, the valve body 630 can be constructed in a position that is exactly as desired for optimum valve performance. Once the valve body 630 has been properly positioned on the form 840 with the leaflet edges 664, 666 pulled through corresponding leaflet slits 694, 696, the leaflet edges 664, 666 are sewn or otherwise attached to the valve body 630 along the slits 694, 696 in any acceptable manner, including methods as discussed above. Additionally, in embodiments in which the commissural tabs were initially only tacked in place, they are then fully secured in place.

Use of the valve assembly tool 830 as discussed above enables consistent and ideal-shaped construction of a valve body in a relatively quick manner. In one embodiment, a method of creating a homologous tissue valve body is provided in which a clinician harvests a patient's own tissue, such as a patient's own pericardium, flattens the homologous source tissue, cuts it according to a desired heart valve pattern, and then assembles the valve body using the valve body assembly tool 830. Preferably, the valve can be created and then implanted by a clinician in the operating room during a single procedure.

Figure 23:
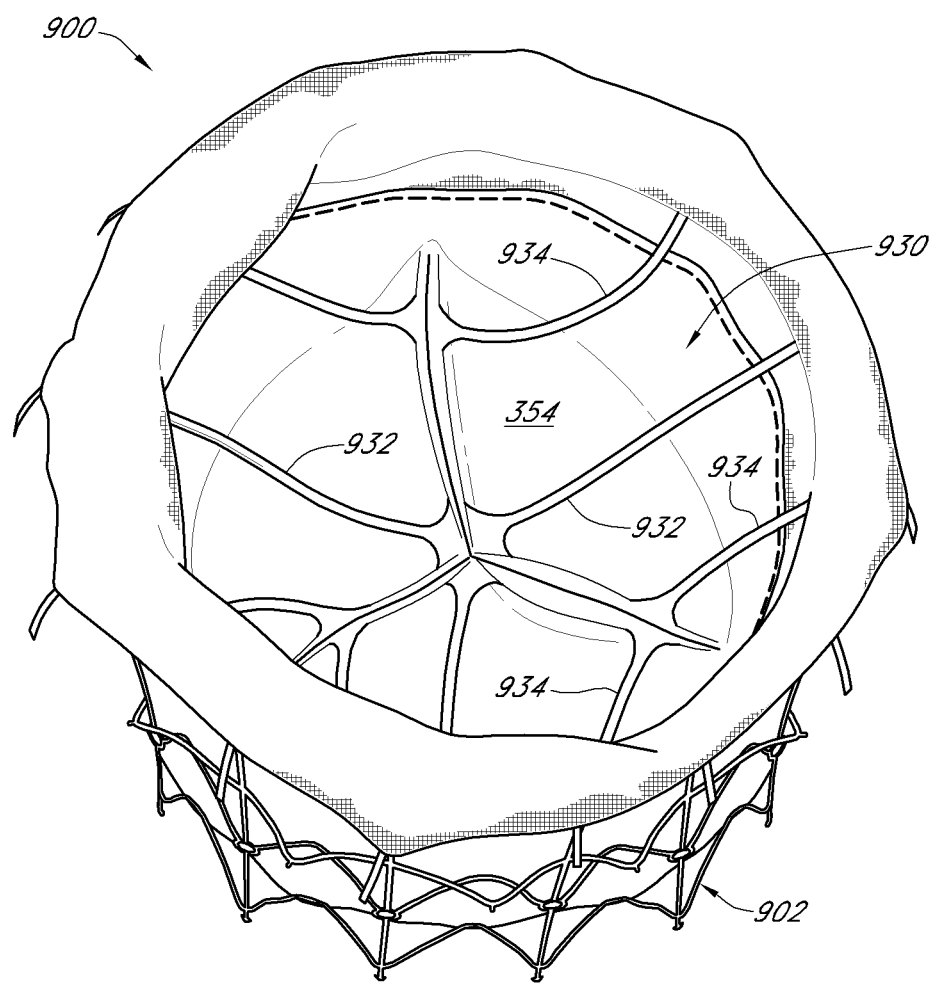
FIG. 23 is a perspective view of an embodiment of a heart valve having a valve body constructed from the pattern of FIG. 22 mounted on a stent.

With reference next to FIG. 23, another embodiment of a valve body 930 can be formed generally using much of the same pattern and manner of construction as discussed above in connection with FIGS. 7-9, with the exception that a plurality of chordae tendinae 932, 934 extend from the downstream edge 362 of each leaflet 354. In the illustrated embodiment, a central and two side chordae 932, 934 are provided. Preferably the central chordae 932 is longer than the side chordae 934. In other embodiments, more or fewer chordae may be provided. In the illustrated embodiment, the chordae 932, 934 are cut as part of the pattern, and thus are contiguous with the associated leaflet 354. Preferably a mount tab 936 is at the tip of each chord 932, 934. The mount tab 936 preferably includes an area of increased diameter that will provide space to accommodate mounting media 938 such as sutures, clips or the like.

FIG. 23 is a schematic representation of a replacement valve 900 employing the valve body 930 attached to a stent 902. Preferably the chordae 932, 934 are attached to the stent 902 downstream of the valve body which, in FIG. 23, is depicted in a closed state. As with natural chordae, preferably the chordae 932, 934 are long enough to allow the leaflets 354 to coapt fully with little or no interference, but also provide distribution of blood pressure forces during pumping of the ventricle. More simply, the chordae communicate blood pressure forces on the leaflets to the frame 902.

With additional reference to FIG. 24, a portion of the stent 902 that can be used to support the valve body 930 and chordae 932, 934 is provided. The illustrated stent is similar to the stent 500 described above. Preferably, a plurality of distal eyelets 940 is formed at or adjacent a distal end 539 of the stent. In the illustrated embodiment, the distal eyelets 940 each have a transversely elongate hole 942 with a generally flat contact surface 944. An attachment eyelet 950 is disposed on the longitudinal struts 530, preferably on the ring 522*c* that includes the apical anchors 550.

With specific reference to FIG. 25, a schematic representation is shown depicting a portion of the valve body 930, stent 902 and chordae 932, all in section. As shown, preferably a downstream end of the valve body is attached via sutures to the second eyelets 546 similar to embodiments discussed above. The valve body leaflets 354 are shown schematically, in phantom lines, and in a coapted state. In the illustrated embodiment, the chordae 932 extends from the leaflet and through the downstream eyelet 940. In some embodiments, the chordae can be sewn to the downstream eyelet 940. However, in the illustrated embodiment, the chordae extends through the eyelet, engages the contact surface 944, reverses course, and extends to the attachment eyelet 950. Preferably, the mount tab 936 of the chordae 932 is attached to the attachment eyelet 950 with, for example, a suture 938. In this manner, as forces from blood pressure push against the coapted leaflets of the closed valve, the chordae distribute such forces to the downstream end of the foreshortening portion of the stent and also to the upstream end of the foreshortening portion of the stent, not only distributing forces from the leaflets, but also encouraging the stent anchors 550, 570 into even more firm and secure grasping of the native valve annulus. Of course, it is to be understood that other specific areas of attachment of the chordae can be employed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. In fact, the embodiments specifically disclosed herein have been used as a vehicle to describe certain inventive features that could be employed in multiple embodiments. Thus, it is contemplated that various combinations or subcombinations of the specific features and aspects of the embodiments may be made and still fall within the scope of the invention. For example, the valve body of FIGS. 7-9 has been described in an embodiment in which adjacent commissural tabs are cut (see FIG. 9A) and in another embodiment in which commissural connections between leaflets are not cut (see FIG. 9B). However, the discussion connected with the valve body embodiment in FIG. 10 does not specifically describe an embodiment in which the commissural connections between leaflets are not cut. Since Applicant contemplates combining and/or substituting features of the discussed embodiments, it should be understood that Applicant also contemplates a variation of the FIG. 10 valve body which employs uncut commissural connections. This example applies to all of the features described herein in connection with specific embodiments. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A prosthesis configured to be deployed within a patient's mitral valve having a mitral annulus, the prosthesis comprising:
an expandable frame comprising a proximal end and a distal end and a longitudinal axis extending therethrough, the frame configured to radially expand and collapse for deployment within the mitral valve;
a plurality of proximal anchors each connected to the frame so that when the frame is in an expanded configuration, outermost ends of the proximal anchors are positioned radially outward from the frame and configured to be positioned on an atrial side of the mitral annulus; and
a plurality of distal anchors each connected to the frame so that when the frame is in an expanded configuration, the distal anchors curve radially outwardly and have outermost ends that are positioned radially outward from the frame and extend generally proximally so that the outermost ends of the distal anchors are proximal to where the distal anchors connect to the frame, the plurality of distal anchors each comprising a tip that extends proximally and substantially parallel to the longitudinal axis of the frame when the frame is in an expanded configuration, the distal anchors configured to be positioned on a ventricular side of the mitral annulus;
a valve body attached to the frame, wherein the valve body can move between (i) an open position wherein blood can flow from the proximal end toward the distal end to allow blood to flow from the left atrium to the left ventricle, and (ii) a closed position which blocks blood from flowing from the distal end toward the proximal end to block blood from flowing from the left ventricle to the left atrium;

wherein the outermost ends of the proximal anchors are circumferentially offset from the outermost ends of the distal anchors when the frame is in an expanded configuration; and wherein the frame is configured such that radial expansion of the frame causes the proximal anchors and the distal anchors to draw closer together.

2. The prosthesis of claim 1, wherein the proximal anchors extend radially outwardly from the frame and comprise tips that extends distally when the frame is in an expanded configuration.

3. The prosthesis of claim 1, wherein the proximal anchors comprise protuberances extending from free apices of adjacent struts.

4. The prosthesis of claim 1, wherein the frame comprises a foreshortening portion.

5. The prosthesis of claim 4, wherein the distal anchors are connected to the foreshortening portion.

6. The prosthesis of claim 5, wherein the proximal anchors are connected to the foreshortening portion.

7. The prosthesis of claim 5, wherein the frame comprises a non-foreshortening portion and the proximal anchors are connected to the non-foreshortening portion.

8. The prosthesis of claim 1, wherein the frame comprises a material capable of self-expansion.

9. The prosthesis of claim 1, wherein the distal anchors are covered with a fabric portion to prevent direct engagement of the distal anchors with tissue.

10. A prosthesis configured to be deployed within a body cavity, the prosthesis comprising:

an expandable frame comprising a proximal end and a distal end and a longitudinal axis extending therethrough, the frame configured to radially expand and contract for deployment within the body cavity, wherein the frame comprises a foreshortening portion and a non-foreshortening portion, wherein:

the foreshortening portion comprises a plurality of interconnected cells having a proximal end and a distal end; and the non-foreshortening portion comprising a plurality of struts having at least a portion thereof extending longitudinally so that the non-foreshortening portion is not substantially expandable in a longitudinal direction, the struts having distal ends that are connected to the proximal ends of the cells, wherein the portion of each of the struts that extends longitudinally extends only longitudinally for substantially the entire distance between the proximal ends of the cells and the proximal end of the frame;

a plurality of proximal anchors each connected to the non-foreshortening portion of the frame so that when the frame is in an expanded configuration, outermost portions of the proximal anchors are positioned radially outward from the frame; and a plurality of distal anchors each connected to the foreshortening portion of the frame so that when the frame is in an expanded configuration, outermost portions of the distal anchors are positioned radially outward from the frame and extend proximally and substantially parallel to the longitudinal axis of the frame when the frame is in an expanded configuration;

wherein the frame is configured such that radial expansion of the frame causes the proximal anchors and the distal anchors to draw closer together.

11. The prosthesis of claim 10, wherein the foreshortening portion is located in a distal portion of the frame and the non-foreshortening portion is located at least in a proximal portion of the frame.

12. The prosthesis of claim 10, wherein when the frame is in an expanded configuration, the proximal anchors extend radially outwardly from the frame and comprise tips that extend distally, and the distal anchors extend radially outwardly from the frame and comprise tips that extend proximally.

13. The prosthesis of claim 10, wherein the proximal anchors comprise protuberances extending from free apices of adjacent struts.

14. The prosthesis of claim 10, wherein the frame comprises a material capable of self-expansion.

15. The prosthesis of claim 10, further comprising a valve body attached to the frame.

16. The prosthesis of claim 10, wherein the non-foreshortening portion comprises at least one row of circumferentially expansible elements, and wherein the struts extend transversely across the at least one row.

17. The prosthesis of claim 10, wherein the struts extend longitudinally over a length that is greater than the length of at least one cell.

18. The prosthesis of claim 10, wherein for each of the plurality of struts, the portion that extends longitudinally and the longitudinal axis both lie entirely within a common plane.

19. The prosthesis of claim 10, wherein the proximal anchors are connected to the non-foreshortening portion of the frame at a junction between the non-foreshortening portion and the foreshortening portion.

20. The prosthesis of claim 10, wherein the proximal anchors are connected to the non-foreshortening portion of the frame at a location on the struts proximally spaced from a junction between the non-foreshortening portion and the foreshortening portion.

21. The prosthesis of claim 10, wherein each of the proximal anchors comprises at least a first strut and a second strut joined together to form a V-shape.

22. The prosthesis of claim 1, wherein the proximal anchors extend generally distally so that the outermost ends of the proximal anchors are distal to where the proximal anchors connect to the frame.

23. The prosthesis of claim 1, wherein the proximal anchors extend longitudinally in a generally distal direction.

24. The prosthesis of claim 1, wherein each of the proximal anchors comprises at least a first strut and a second strut joined together to form a V-shape.

25. The prosthesis of claim 1, wherein each of the proximal anchors is connected to struts of the frame that have at least a portion thereof extending longitudinally.

26. The prosthesis of claim 1, wherein the distal anchors extend longitudinally in a generally proximal direction.

* * * * *